US012388948B2

(12) United States Patent
Park et al.

(10) Patent No.: US 12,388,948 B2
(45) Date of Patent: Aug. 12, 2025

(54) SYSTEMS INCLUDING PORTABLE PHOTO STUDIOS

(71) Applicant: Verily Life Sciences LLC, South San Francisco, CA (US)

(72) Inventors: Angela Park, San Francisco, CA (US); Jonathan Grossman, San Francisco, CA (US)

(73) Assignee: Verily Life Sciences LLC, Dallas, TX (US)

( * ) Notice: Subject to any disclaimer, the term of this patent is extended or adjusted under 35 U.S.C. 154(b) by 0 days.

(21) Appl. No.: 18/374,499

(22) Filed: Sep. 28, 2023

(65) Prior Publication Data

US 2024/0031520 A1 Jan. 25, 2024

Related U.S. Application Data

(62) Division of application No. 17/450,043, filed on Oct. 5, 2021, now Pat. No. 11,778,133, which is a division
(Continued)

(51) Int. Cl.
*H04N 5/28* (2006.01)
*G06F 16/54* (2019.01)
(Continued)

(52) U.S. Cl.
CPC ............ *H04N 5/28* (2013.01); *G06F 16/54* (2019.01); *G16H 30/20* (2018.01); *G16H 40/67* (2018.01);
(Continued)

(58) Field of Classification Search
CPC ....... G06F 16/54; G06F 16/587; G16H 10/20; G16H 30/20; G16H 30/40; G16H 40/63;
(Continued)

(56) References Cited

U.S. PATENT DOCUMENTS 6,085,195 A * 7/2000 Hoyt .................. G03B 17/53
6,086,380 A * 7/2000 Chu .................... G07F 17/26
(Continued)

FOREIGN PATENT DOCUMENTS

CN 201011545 Y 1/2008
CN 105824171 A 8/2016
(Continued)

OTHER PUBLICATIONS

U.S. Appl. No. 16/733,898, Non-Final Office Action mailed on Dec. 4, 2020, 13 pages.
(Continued)

*Primary Examiner* — Mainul Hasan
(74) *Attorney, Agent, or Firm* — Kilpatrick Townsend & Stockton LLP

(57) ABSTRACT

A portable photo studio system includes a portable photo studio and an electronic device such as a camera-enabled smartphone. A computer system is provided that interacts with the electronic device. The computer system requests an image capture system. In response, the electronic device captures image data and shares it with the computer system. The computer system then analyzes the image data to identify areas of interest.

20 Claims, 15 Drawing Sheets

Related U.S. Application Data of application No. 16/733,907, filed on Jan. 3, 2020, now Pat. No. 11,159,747.

(51) Int. Cl.
| | |
|---|---|
| *G16H 30/20* | (2018.01) |
| *G16H 40/67* | (2018.01) |
| *H04N 7/18* | (2006.01) |
| *H04N 23/54* | (2023.01) |
| *H04N 23/56* | (2023.01) |

(52) U.S. Cl.
CPC ............ *H04N 7/183* (2013.01); *H04N 23/54* (2023.01); *H04N 23/56* (2023.01)

(58) Field of Classification Search
CPC ........ G16H 40/67; G16H 80/00; H04N 23/50; H04N 23/54; H04N 23/56; H04N 5/28; H04N 7/183
See application file for complete search history.

(56) References Cited

U.S. PATENT DOCUMENTS

| | | | |
|---|---|---|---|
| 6,354,486 B1 | 3/2002 | Ho | |
| 6,798,443 B1* | 9/2004 | Maguire, Jr. | G06F 3/016 |
| | | | 348/121 |
| 8,233,785 B1* | 7/2012 | Surma | G03D 15/005 |
| | | | 396/1 |
| 8,269,900 B2* | 9/2012 | O'Connell | H04N 5/222 |
| | | | 353/50 |
| 8,457,480 B1* | 6/2013 | Surma | H04N 17/002 |
| | | | 396/1 |
| 8,508,572 B2* | 8/2013 | Ryckman | H04N 7/15 |
| | | | 348/14.08 |
| 8,610,777 B2 | 12/2013 | Bengtsson | |
| 8,763,888 B2 | 7/2014 | Willman et al. | |
| 8,957,942 B2* | 2/2015 | Ryckman | G16H 80/00 |
| | | | 386/224 |
| 9,259,842 B2* | 2/2016 | Fouillade | B25J 19/023 |
| 9,360,737 B2 | 6/2016 | Johnson et al. | |
| 9,513,537 B2 | 12/2016 | Mun et al. | |
| 9,578,188 B1* | 2/2017 | Kircher | H04N 23/632 |
| 10,264,250 B2 | 4/2019 | Maltz et al. | |
| 10,554,929 B2* | 2/2020 | Stephens | H04L 51/10 |
| 11,049,272 B1* | 6/2021 | Benson | G03B 15/02 |
| 11,159,747 B2* | 10/2021 | Park | G16H 30/20 |
| 11,204,538 B2* | 12/2021 | Park | G03B 15/00 |
| 11,778,133 B2 | 10/2023 | Park et al. | |
| 2008/0055398 A1* | 3/2008 | Ryckman | H04N 5/272 |
| | | | 348/14.1 |
| 2008/0068473 A1* | 3/2008 | Ryckman | G10H 1/365 |
| | | | 348/E5.022 |
| 2008/0074487 A1* | 3/2008 | Ryckman | G03B 17/53 |
| | | | 348/14.1 |
| 2008/0075436 A1* | 3/2008 | Ryckman | G07F 17/3206 |
| | | | 348/14.1 |
| 2008/0115181 A1* | 5/2008 | Ryckman | G10H 1/361 |
| | | | 348/E7.079 |
| 2010/0007665 A1* | 1/2010 | Smith | G06T 13/40 |
| | | | 345/473 |
| 2010/0134695 A1* | 6/2010 | O'Connell | G03B 35/00 |
| | | | 348/789 |
| 2011/0069944 A1* | 3/2011 | Johnson | G03B 15/00 |
| | | | 396/2 |
| 2011/0081140 A1* | 4/2011 | Messier | G03B 17/53 |
| | | | 396/2 |
| 2011/0149248 A1* | 6/2011 | Ley | H04N 5/272 |
| | | | 352/43 |
| 2012/0140098 A1* | 6/2012 | Ryckman | G07F 17/3223 |
| | | | 348/241 |
| 2012/0316676 A1* | 12/2012 | Fouillade | B25J 13/003 |
| | | | 901/1 |
| 2014/0002868 A1 | 1/2014 | Landa et al. | |
| 2014/0125829 A1* | 5/2014 | Hashiguchi | H04N 23/66 |
| | | | 348/211.99 |
| 2015/0042822 A1* | 2/2015 | Le | H04N 23/56 |
| | | | 348/370 |
| 2015/0186743 A1* | 7/2015 | Karnos | H04N 23/70 |
| | | | 382/195 |
| 2016/0202599 A1* | 7/2016 | Bochenek | G03B 17/56 |
| | | | 396/4 |
| 2016/0205354 A1* | 7/2016 | Stephens | H04N 21/4786 |
| | | | 386/282 |
| 2017/0163937 A1* | 6/2017 | McNelley | H04N 7/144 |
| 2017/0244909 A1* | 8/2017 | Dannen | H04N 5/28 |
| 2017/0251172 A1* | 8/2017 | McNelley | G09G 5/00 |
| 2017/0339350 A1* | 11/2017 | Üstün | B60P 3/14 |
| 2018/0084224 A1* | 3/2018 | McNelley | H04N 7/15 |
| 2018/0153443 A1* | 6/2018 | Hilton | A61B 5/1077 |
| 2018/0176506 A1* | 6/2018 | McNelley | H04N 7/142 |
| 2018/0347805 A1* | 12/2018 | Abou-Fadel | G06F 1/1632 |
| 2018/0376225 A1* | 12/2018 | Jones | G10H 1/368 |
| 2019/0141291 A1* | 5/2019 | McNelley | H04N 9/3185 |
| 2019/0227419 A1* | 7/2019 | McNelley | H04N 9/3182 |
| 2019/0294031 A1* | 9/2019 | Ley | H04N 5/2621 |
| 2020/0244934 A1* | 7/2020 | Wu | H04N 9/3194 |
| 2021/0201492 A1* | 7/2021 | Yeates | G16H 30/20 |
| 2021/0208484 A1* | 7/2021 | Park | G03B 15/00 |
| 2021/0211588 A1* | 7/2021 | Park | G06F 16/587 |
| 2021/0241444 A1* | 8/2021 | Cyrus | G06T 7/0002 |
| 2022/0030182 A1 | 1/2022 | Park et al. | |
| 2024/0031520 A1* | 1/2024 | Park | G06F 16/54 |

FOREIGN PATENT DOCUMENTS

| | | | | |
|---|---|---|---|---|
| JP | | 3097131 U | 1/2004 | |
| WO | WO-2021138439 A1 * | | 7/2021 | ............ G03B 15/00 |

OTHER PUBLICATIONS

U.S. Appl. No. 16/733,898, Notice of Allowance mailed on Aug. 6, 2021, 5 pages.
U.S. Appl. No. 16/733,907, Non-Final Office Action mailed on Nov. 17, 2020, 15 pages.
U.S. Appl. No. 16/733,907, Notice of Allowance mailed on Jun. 7, 2021, 11 pages.
U.S. Appl. No. 17/450,043, Non-Final Office Action mailed on Dec. 6, 2022, 16 pages.
U.S. Appl. No. 17/450,043, Notice of Allowance mailed on May 24, 2023, 11 pages.
International Application No. PCT/US2020/067491, International Search Report and Written Opinion mailed on May 5, 2021, 17 pages.
International Application No. PCT/US2020/067491, Invitation to Pay Additional Fees And, Where Applicable, Protest Fee mailed on Mar. 3, 2021, 2 pages.

* cited by examiner

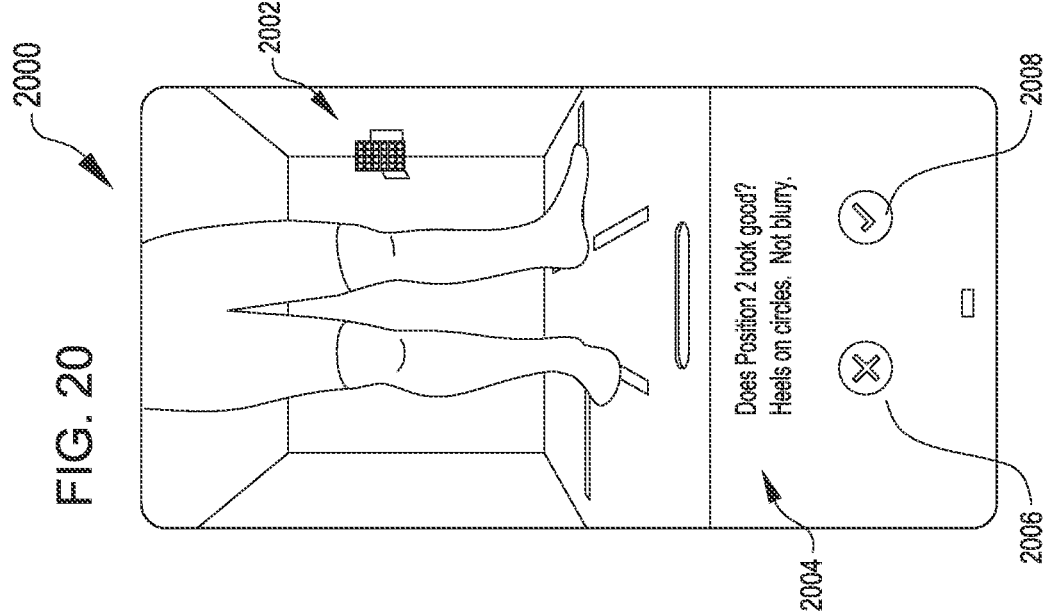
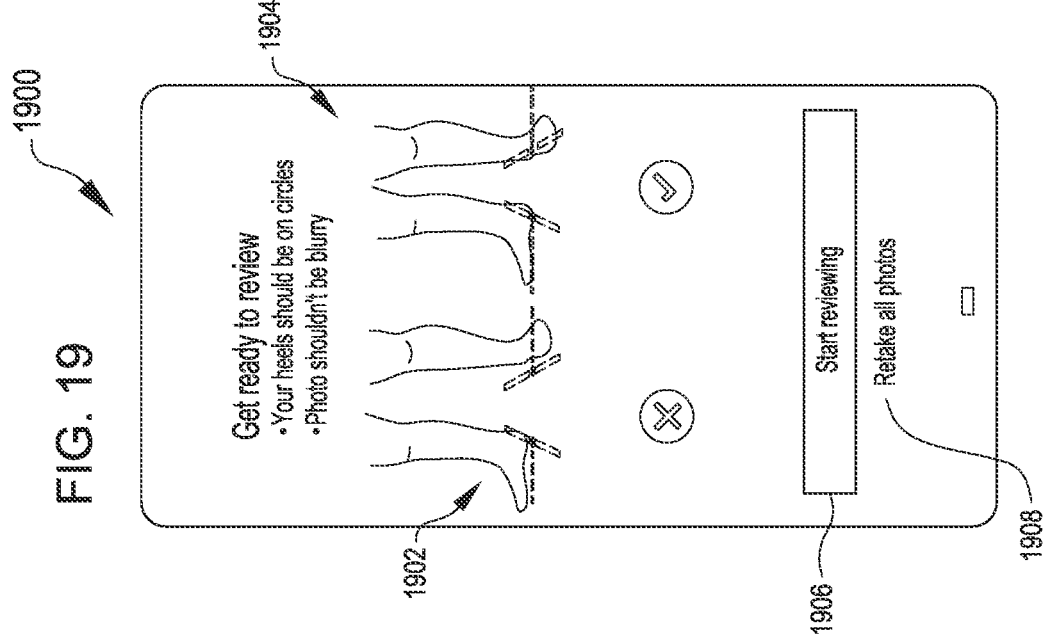

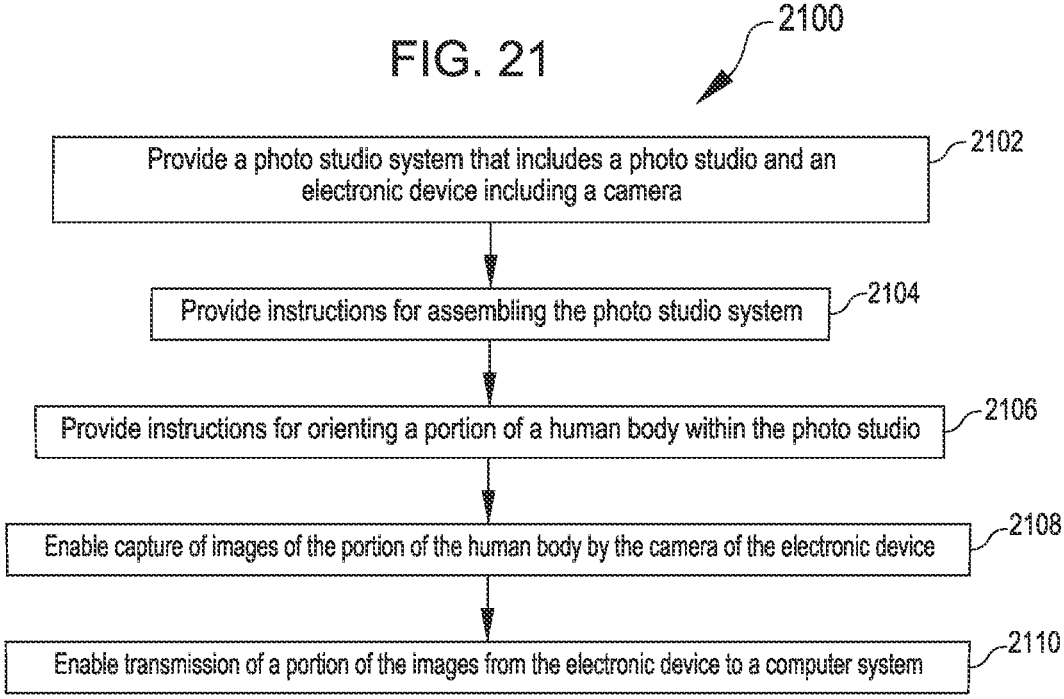
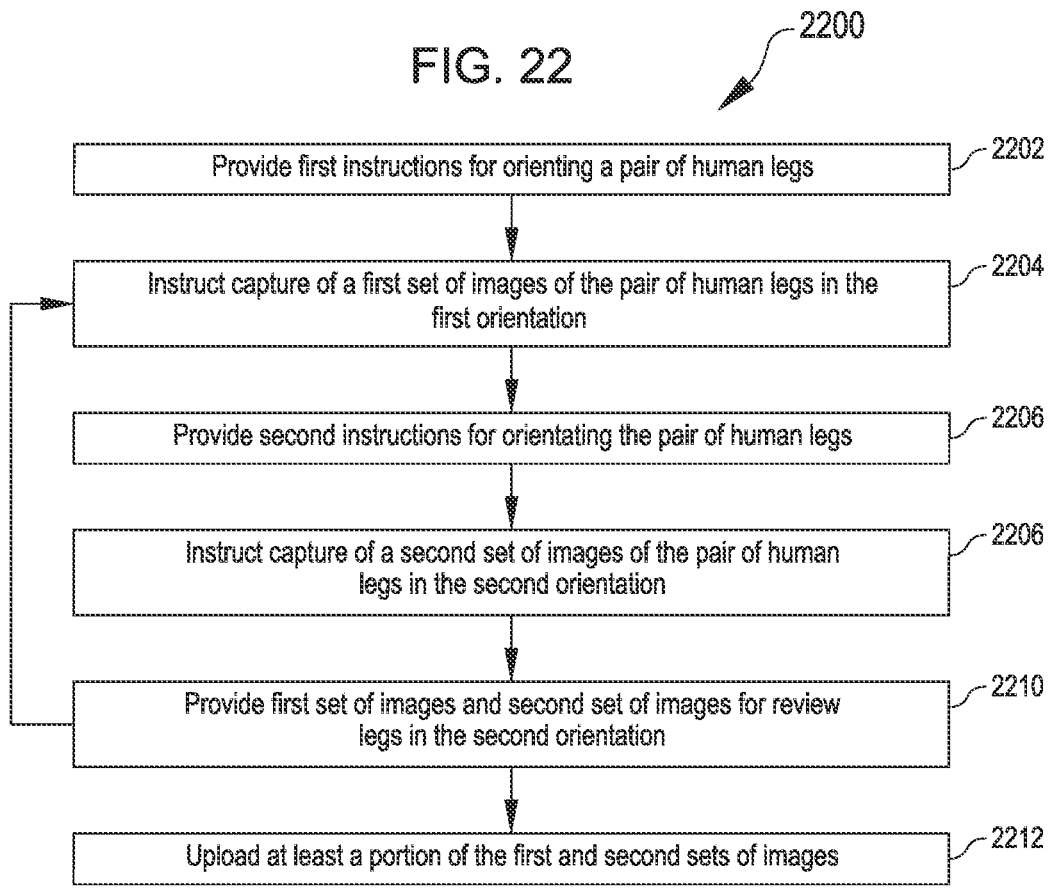

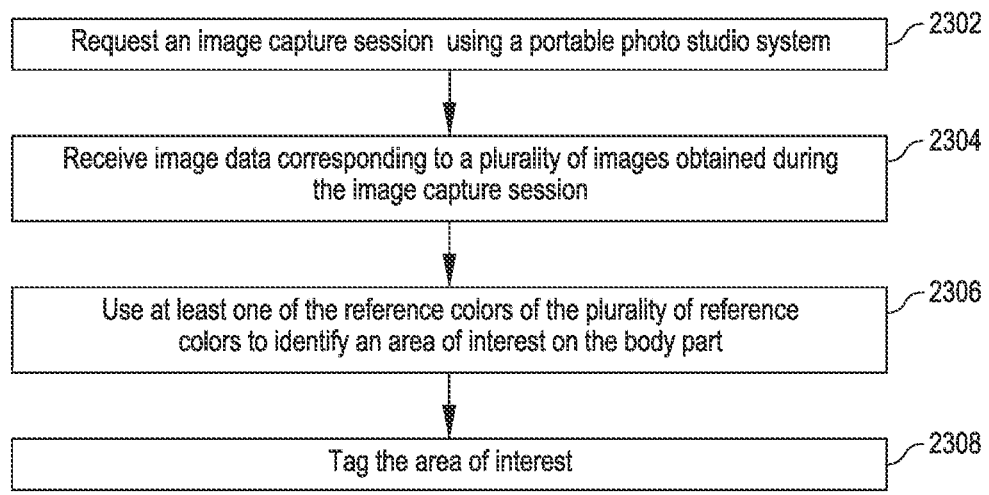
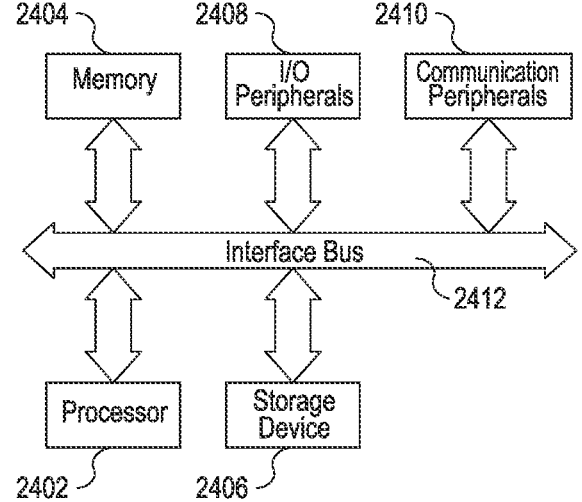

SYSTEMS INCLUDING PORTABLE PHOTO STUDIOS

CROSS-REFERENCE TO RELATED APPLICATIONS

This application is a divisional of U.S. patent application Ser. No. 17/450,043 filed Oct. 5, 2021, titled "Systems Including Portable Photo Studios", which application is a divisional of U.S. patent application Ser. No. 16/733,907 filed Jan. 3, 2020, titled "Systems Including Portable Photo Studios", now U.S. Pat. No. 11,159,747; which application is related to U.S. patent application Ser. No. 16/733,898, filed Jan. 3, 2020, titled "Portable Photo Studios," the entireties of which are hereby incorporated by reference.

BACKGROUND

Telemedicine includes the remote diagnosis and treatment of patients using telecommunications technology. For example, a patient may interact with a clinician in real-time (e.g., over the phone, using a messaging application, or using video conferencing tools) or by storing and forwarding digital images of visible symptoms to the clinician (store and forward approach (SAF)). A subspecialty of telemedicine is teledermatology, which deals with the diagnosis and treatment of skin conditions. Teledermatology is practiced primarily using the SAF approach. While cameras, including those included in mobile devices, have become ubiquitous, the clinical value of images captured by these cameras is unclear given the varying conditions under which the images are captured (e.g., differences in lighting conditions, camera settings, post processing, etc.) and the quality of the camera sensors themselves.

Participants in clinical studies, especially those dealing with skin conditions, may be required to visit a clinic or other location away from their homes to have images taken of the areas of interest on their bodies in a controlled environment. The controlled environment includes consistent conditions under which the images are taken, which results in images that can be reliable compared to others taken in the same controlled environment. The requirement of traveling to the clinic and having images taken in the controlled environment, however, may become too inconvenient to some participants, which may result in abandonment by participants.

BRIEF SUMMARY

Various examples are described relating to portable photo studios, systems that include portable photo studios, and methods including the use of portable photo studios.

One general aspect includes an apparatus, including: a bottom including a first edge. The apparatus also includes a first side wall pivotably connected to the bottom at a first hinge. The apparatus also includes a second side wall pivotably connected to the first side wall at a second hinge. The apparatus also includes a third side wall pivotably connected to the first side wall at a third hinge, the third hinge opposite the second hinge, where the first side wall, the second side wall, and the third side wall are respectively pivotable about the first hinge, the second hinge, and the third hinge between an unassembled state and an assembled state in which the first side wall, the second side wall, and the third side wall form a U shape. The apparatus also includes an electronics stand pivotably connected to the first edge at a fourth hinge, the electronics stand including a pocket sized and configured to receive and support an electronic device, where the electronics stand is pivotable about the fourth hinge between the unassembled state and the assembled state in which the electronics stand faces the U shape.

Another general aspect includes a method of setting up a portable photo studio, including rotating, at a first hinge, a first part of a bottom of the portable photo studio into an open position. The portable photo studio includes the bottom, a background section including a first wall, a second wall, and a third wall; and an electronics stand. The method also includes rotating, at a second hinge, the background section into an open position, where the second hinge is integrally formed between a second part of the bottom and the first wall. The method also includes rotating, at a third hinge, the second wall into an open position, where the third hinge is integrally formed between the first wall and the second wall. The method also includes rotating, at a fourth hinge, the third wall into an open position, where the fourth hinge is integrally formed between the first wall and the third wall. The method also includes rotating, at a fifth hinge, the electronics stand into an open position, where the fifth hinge is integrally formed between the first part of the bottom and the electronics stand.

Another general aspect includes a method of setting up a portable photo studio, including rotating, at a first hinge integrally formed in the portable photo studio, a first part of a bottom section of the portable photo studio. The method also includes rotating, at a plurality of hinges integrally formed in the portable photo studio, a background section of the portable photo studio to define a U-shaped cavity, where at least two edges of the background section physically contact the bottom section when the background section defines the U-shaped cavity. The method also includes rotating, at a second hinge, an electronics stand into an orientation that opposes the U-shaped cavity, where the second hinge is integrally formed between the first part of the bottom section and the electronics stand.

Another general aspect includes a method of forming a portable photo studio, including providing a piece of planar material. The method also includes forming, in the piece of planar material, a background section including a plurality of panels, a bottom section connected to the background section, and an electronics stand connected to the bottom section. The method also includes forming, in the piece of planar material, a first hinge between the bottom section and a first panel of the plurality of panels. The method also includes forming, in the piece of planar material, a second hinge between the first panel and a second panel of the plurality of panels. The method also includes forming, in the piece of planar material, a third hinge between the first panel and a third panel of the plurality of panels. The method also includes forming, in the electronics stand of the piece of planar material, a pair of support stands and a pocket configured to receive and support an electronic device. The method also includes forming, in the piece of planar material, a fourth hinge between the bottom section and the electronics stand.

Another general aspect includes an apparatus, including light-reflecting means for reflecting light during image capturing. The apparatus also includes supporting means for supporting an electronic device and orienting a camera of the electronic device towards the light-reflecting means. The apparatus also includes supporting means for supporting a light source oriented towards the reflecting means. The apparatus also includes orienting means for directing orientations of a user with respect to the supporting means.

Another general aspect includes a system, including: a portable photo studio, an electronics stand, and an electronic device. The portable photo studio includes a bottom section, a background section pivotably connected to the bottom section and including a plurality of walls that are pivotable with respect to each other to define a U shape. The electronics stand is pivotably connected to the bottom section and pivotable with respect to the bottom section into an upright orientation that opposes the U shape. The electronics stand includes a mounting pocket. The electronic device is removably mountable within the mounting pocket of the electronics stand, where the electronic device, when mounted in the mounting pocket, orients a camera of the electronic device toward the U shape.

Another general aspect includes a method, including: providing a photo studio system that includes a photo studio and an electronic device including a camera. The method also includes providing instructions for assembling the photo studio system. The method also includes providing instructions for orienting a portion of a human body within the photo studio. The method also includes enabling capture of images of the portion of the human body by the camera of the electronic device. The method also includes enabling transmission of a portion of the images from the electronic device to a computer system.

Another general aspect includes a computer-implemented method, including providing, by an electronic device of a portable photo studio system, first instructions for orientating a pair of human legs into a first orientation with respect to a set of orientation indicia of a portable photo studio of the portable photo studio system. The computer-implemented method also includes capturing, by a camera of the electronic device, a first set of images of the pair of human legs in the first orientation. The computer-implemented method also includes providing, by the electronic device, second instructions for orientating the pair of human legs into a second orientation with respect to the set of orientation indicia. The computer-implemented method also includes capturing, by the camera of the electronic device, a second set of images of the pair of human legs in the second orientation. The computer-implemented method also includes uploading, by the electronic device and to an external system, at least a portion of the first set of images and the second set of images. Other embodiments of this aspect include corresponding computer systems, apparatus, and computer programs recorded on one or more computer storage devices, each configured to perform the actions of the methods.

One general aspect includes a computer-implemented method, including requesting an image capture session using a portable photo studio system that includes a portable photo studio apparatus forming a unicolor background, an electronic device removably mountable to the portable photo studio apparatus, and a color card mountable to the portable photo studio apparatus in an orientation that opposes the electronic device, the color card including a plurality of reference colors. The computer-implemented method also includes receiving, from the electronic device, image data corresponding to a plurality of images obtained during the image capture session, the image data, for each image of the plurality of images, representing at least (i) a human body part in an orientation, (ii) the color card including the plurality of reference colors, and (iii) the unicolor background in front of which the human body part is positioned. The computer-implemented method also includes using at least one of the reference colors of the plurality of reference colors to identify an area of interest on the body part. Other embodiments of this aspect include corresponding computer systems, apparatus, and computer programs recorded on one or more computer storage devices, each configured to perform the actions of the methods.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

FIG. 19 illustrates an instruction user interface view of a portable photo studio application for use with a portable photo studio system, according to at least one example;

FIG. 20 illustrates a quality control user interface view of the photo studio application of FIG. 19, according to at least one example;

FIG. 21 illustrates a flow chart showing a process for obtaining images of a human body using a portable photo studio system, according to at least one example;

FIG. 22 illustrates a flow chart showing a process for obtaining images of a human body using a portable photo studio system, according to at least one example;

FIG. 23 illustrates a flow chart showing a process for conducting an image capture session using a portable photo studio system and evaluating images of an area of interest, according to at least one example; and FIG. 24 illustrates a generic computing device for interacting with a portable photo studio system, according to at least one example.

DETAILED DESCRIPTION

Figure 1:
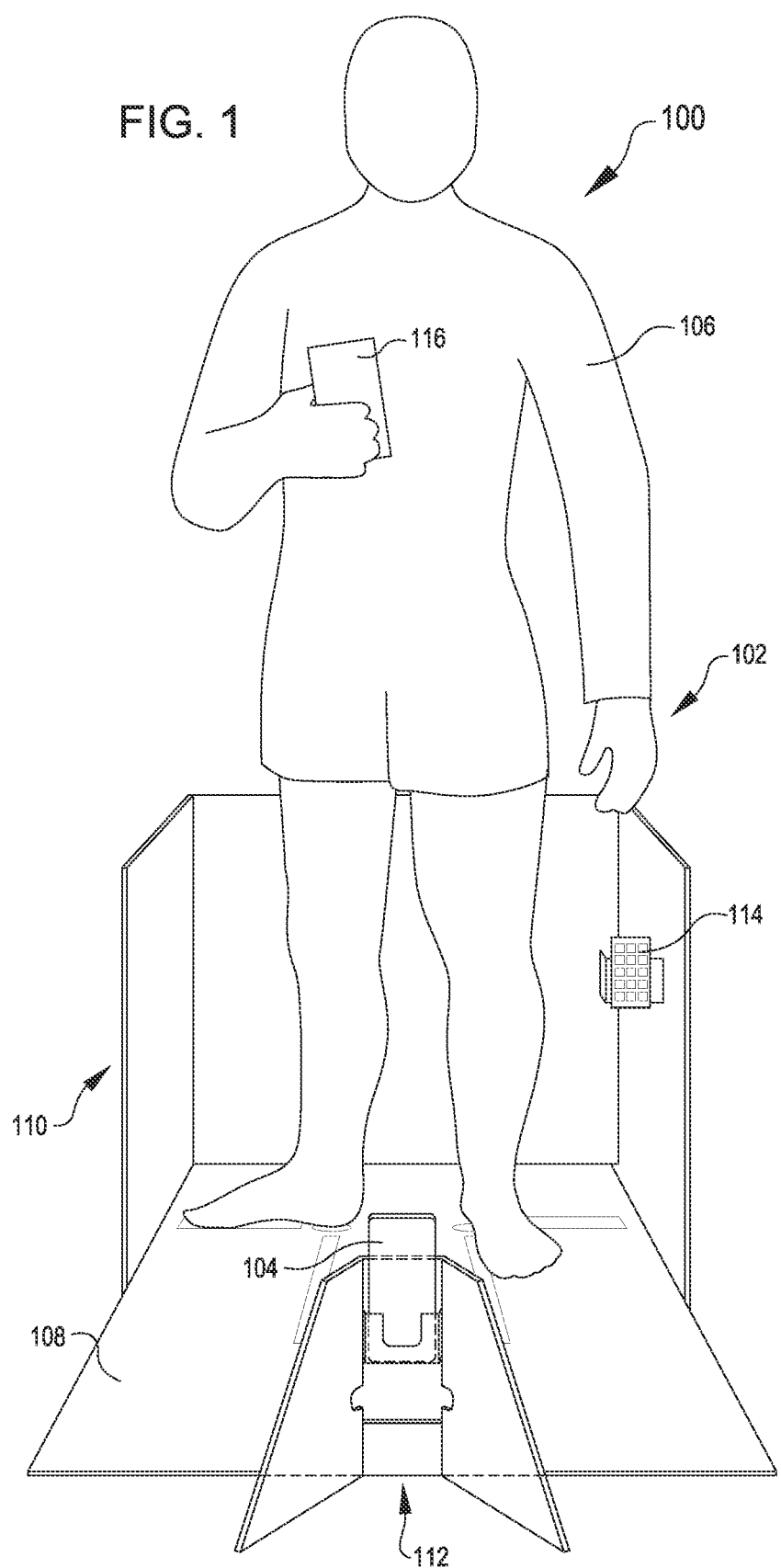
FIG. 1 illustrates a perspective view of a portable photo studio system, according to at least one example.

Examples are described herein in the context of portable photo studio systems that are used to capture consistent and repeatable images of human legs. Those of ordinary skill in the art will realize that the following description is illustrative only and is not intended to be in any way limiting. For example, the features described with respect to capturing images of human legs are applicable to any other appendage or part of a human body. In particular, the portable photo studio systems described herein may be adapted for imaging other parts of the body besides just the legs. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

Examples described herein are directed to portable photo studio systems that include a portable photo studio, an electronic device including a camera, a light source, and a color card. An example portable photo studio system is standalone and designed to enable users (e.g., patients) to obtain images of their legs in the comfort of their homes and at a level of quality that is equal to that of a trained professional taking pictures in a controlled environment outside the home (e.g., at a clinic). This high level of quality is achieved, at least in part, because the example portable photo studio system controls many of the variables that impact image quality. For example, parameters of the camera are known and can be accounted for during later image processing, the camera is held in a fixed orientation (e.g., position, rotation and distance) with respect to object being imaged (e.g., a pair of human legs), the portable photo studio includes a unicolor background that minimizes shadows (e.g., walls painted a particular gray color), the electronic device outputs instructions to the user to correctly orient her legs, and the color card and its standard set of reference colors are used during later image processing to maintain consistency across sets of images.

The example portable photo studio is formed from a single piece of material that can be collapsed into itself for easy transportation. Once at a destination (e.g., a user's home), a portable photo studio may be quickly assembled by unfolding parts of the portable photo studio to form a free-standing U-shaped background and an electronics stand for holding the electronic device in a fixed orientation. To obtain images using the portable photo studio, a user steps into a volume defined by the U-shaped background and the electronic device guides the user through a set of predefined or undefined set of poses. When in the different poses, the electronic device causes the camera to capture images of the user. The user may review the images to confirm the quality thereof. After which, the electronic device may transmit the images to an external computer system for further processing, storage, and tagging.

In an illustrative example, a portable photo studio is described. A user may use the portable photo studio in her home for obtaining images of certain body parts (e.g., the user's legs). For example, the user may be required to provide the images as part of participating in a clinical study, tracking an ongoing treatment, or for any other suitable reason. Using the portable photo studio eliminates the need for the user to leave their home to obtain images because the portable photo studio reduces the number of variables for obtaining high quality and consistent images.

The portable photo studio is formed from a single piece of material (e.g., corrugated cardboard) and includes a bottom section, a background section, and an electronics stand. The background section and the electronics stand are each connected to the bottom section via flexible hinges (e.g., preformed bends in the material). Because of these hinges, the two sections and the electronics stand can be folded together to create a folded package. In the folded package, the portable photo studio takes a thin rectangular shape and reveals an integrated handle. Using the handle, a single user may easily carry the portable photo studio.

To set up the portable photo studio for obtaining photos, the user first places the bottom section of the portable photo studio on the floor. Next, the electronics stand is unfolded from the folded package and placed on the floor. At this point, the electronics stand or the background section may be set up. To set up the background section, which includes three panels and is connected to the bottom section, the background section is unfolded from the folded package. Instead of placing the background section on the floor, the three panels are unfolded so that the three panels are about perpendicular to the bottom section, with bottom edges of the two outside panels being placed adjacent to the bottom section. In this orientation, the background section forms a U-shaped background in an upright position that opens towards the electronics stand. The U-shape also holds the background section in the upright position. To set up the electronics stand, the electronics stand is folded up towards the U-shaped background and a pair of wings are folded out to support the electronics stand in the upright position. At least four sides of the portable photo studio (e.g., the three panels of the background section and the bottom section) may be coated with a particular paint color to provide a standard backdrop for the images.

In another illustrative example, a system including a portable photo studio is described. This system, sometimes referred to as a portable photo studio system, includes the portable photo studio described above, along with other components to enable capturing of consistent images. These components includes a portable electronic device that includes a camera (e.g., a smartphone), a color card, and a light. The portable electronic device is mounted in the electronics stand and oriented with its camera directed towards the U-shaped background. The color card (e.g., a calibration card) is mounted to the portable photo studio at a location within the field of view of the camera, such as on the back wall of the U-shaped background facing the camera. The light is mounted below the electronic device with its light source directed towards the U-shaped background. In this manner, when the user steps into the assembled portable photo studio (e.g., within the volume defined by the three panels of the background section and the bottom section), the light will shine on the user and the color card, and the camera can capture images of the user and the color card. The electronic device includes an application that guides the user during the image capture process. For example, the application may output instructions (e.g., via a speaker) for the user to orient her legs into various poses with respect to markings on the bottom section (e.g., a set of reference indicia). The application may signal the camera to capture images when the user is in the correct pose. In some examples, the user may cause the camera to capture the images (e.g., via a voice command, by using a remote communicatively linked to the camera, by using an application communicatively linked to the camera, or the like). Once a suitable number of images have been obtained, which may be a predefined number, the user may remove the electronic device from the electronics stand and interact with the application. This may include the user confirming whether the images are suitable with respect to some set of standards. If so, the electronic device may transmit the images to another computer system for processing. If the pictures are not suitable, the electronic device may prompt the user to conduct another image capture session.

The portable photo studio system pairs a complete application experience with audio, a the portable folding photo studio, lighting control, and a color calibration tool that enables patients to take high quality images for clinical trials at home. The portable photo studio is foldable for ease of transportation and storage and is scalable up and down for adaptation to imaging different body parts.

The portable photo studio system costs much less than a photo setup in a clinical site. Use of the portable photo studio system enables patients to take high quality photos as part of clinical studies (e.g., to gauge drug efficacy) without the added burden of travel to a clinical site. Additionally, because the system uses an electronic device to guide the patient through the image capture process (instead of a clinician or photographer) some users may be more comfortable with the image capture process. Given the elimination of the travel burden and the ease of conducting image capture sessions stress-free at home, use of the portable photo studio system results in improved patient experience, which directly corresponds to improved adherence and completion rates (e.g., the rates at which patients adhere to and complete clinical studies or treatments).

These illustrative examples are given to introduce the reader to the general subject matter discussed herein and the disclosure is not limited to this example. The following sections describe various additional non-limiting examples of portable photo studios, portable photo studio systems, and corresponding methods.

Referring now to the figures, FIG. 1 illustrates a perspective view of a portable photo studio system 100, according to at least one example. The portable photo studio system 100 includes a portable photo studio 102 and an electronic device 104. In FIG. 1, the portable photo studio 102 is illustrated in an assembled state and may therefore be used by a user 106 to capture images of some portion of her body. Because of the portable nature of the portable photo studio 102, the user 106, either alone or with the help of somebody else, may set up and take down the portable photo studio 102 at various locations (e.g., at a home of the user 106).

The portable photo studio 102 and the electronic device 104 may be provided to the user 106 as part of a clinical study, an ongoing teledermatological treatment, or as part of any other health-related program that could benefit from high quality and consistent images of the user 106. In the illustrated example, the user 106 is shown standing inside the portable photo studio 102 (e.g., on a bottom section 108 and within a background section 110) and the electronic device 104, which includes a camera, is supported by an electronics stand 112 and oriented towards the user 106. The camera is used to capture images of the user's 106 legs. Included in the field of view of the camera is a color card 114 that is mounted to the portable photo studio 102. The color card 114 includes a set of different reference colors that can be referenced during post processing and/or review of the images. In some examples, reference colors from the color card 114 may be printed, painted, or otherwise secured to the background section 110.

In FIG. 1, the user 106 is illustrated as holding another electronic device, referred to herein as a personal electronic device 116. As part of participating in the program that uses the portable photo studio system 100, the user 106 may download an application onto the personal electronic device 116. Generally, the application may manage aspects of the program, e.g., notifying the user 106 via the personal electronic device 116 when it is time to conduct an image capture session. The personal electronic device 116 may be in network communication with the electronic device 104. For example, the personal electronic device 116 may send a signal to the electronic device 104 requesting the electronic device 104 to initiate an image capture session. In some examples, performance of the image capture session may be distributed between the personal electronic device 116 and the electronic device 104. For example, instructions for orienting the user's 106 body may be presented at the personal electronic device 116 and the electronic device 104 may be used to capture the images, e.g., responsive to receiving an image capture signal from the personal electronic device 116. In some examples, the user 106 may trigger the electronic device 104 to capture images, e.g., by the user 106 selecting a button on the personal electronic device 116 that causes the electronic device 104 to capture the images, via a voice command (e.g., "take photo"), etc. The voice commands may also be used to initiate and end image capture sessions, to retake photos, and the like.

The image capture sessions may be performed at some predefined interval (e.g., every few hours, every day, every week, etc.), at certain times of day (e.g., morning, afternoon, and evening), responsive to triggers (e.g., when a clinician requests an image via a corresponding application that communicates with the application on the personal electronic device 116), and in any other suitable manner. When the user 106 gets the notification on the personal electronic device 116, the user 106 may then interact with an application on the electronic device 104. The application on the electronic device 104 may guide the user 106 through the image capture process by providing instructions for poses, automatically capturing images of the user 106 in various poses, performing a quality control check, and transmitting the images to an external computing system (e.g., a server computer) for review and/or processing.

In some examples, the photo studio system 102 may also include a remote for controlling the electronic device 104. This remote, which may communicate with the electronic device 104 via a wireless network such as a Bluetooth® network, may be used by the user 106 to operate the camera of the electronic device 104. For example, the application on the electronic device 104 may instruct the user 106 to orient her body into certain poses and the user 106 may decide when to capture the images by operating the remote. In some examples, the user 106 may use the personal electronic device 116 like a remote to control the camera of the electronic device 104. For example, the application on the electronic device 104 may instruct the user 106 to orient her body into certain poses and the user 106 may decide when to capture the images by operating the personal electronic device 116.

In some examples, a clinician or other user may capture images of the user 106 in real-time. For example, the clinician may user a clinician interface to remotely connect (e.g., via video chat) to the electronic device 104. At this point, the clinician may provide orientation instructions, capture images of the user 106, review quality of the images, and instruct the user 106 to retake poor quality photos.

In some examples, a secondary person such as a caretaker or family member may capture images of the user while the user is standing within the portable photo studio 102. For example, the electronic device 104 may include photo capture buttons such as pause, resume, skip, or retake, along with timers to the interface, and the secondary person may use the electronic device 104 including these buttons to capture the images of the user 106.

In some examples, the user portable photo studio system 100 may include multiple electronic devices 104 each including one or more cameras. The multiple electronic devices 104 may be mounted at different locations within the portable photo studio system 100 to capture different perspectives of the user 106. In this example, the portable photo studio system 100 may also include a tablet or other electronic device including a screen at which one or more views from the electronic devices 104 may be presented (e.g., see what the cameras see).

In some examples, the user 106 may view a screen of the electronic device 104 as the user 106 orients into the correct positions. On the screen of the electronic device 104 may be presented a body outline that may include feedback to guide the user into the correct positions.

In some examples, the portable photo studio system 100 may also include a mirror disposed adjacent to the electronics stand 112. The mirror may be arranged to reflect the screen back to the user 106 so that the user standing at a distance away from the electronic device 104 can see the screen when the camera on the back of the electronic device 104 is being used.

In some examples, the portable photo studio system 100 may also include a track that extends radially about the portable photo studio 102. The track may be configured to move the electronic device 104 radially with respect to the user 106. For example, the electronic device 104 may be mounted to the track and/or a car mounted upon the track that travels radially about the user 106 and "scan" the body (e.g., capture multiple images and/or video).

In some examples, the electronic device 104 may capture video of the user 106 instead of or in addition to the images. In some examples, the electronic device 104 may take a panorama interstitial image of the body area.

Figure 2:
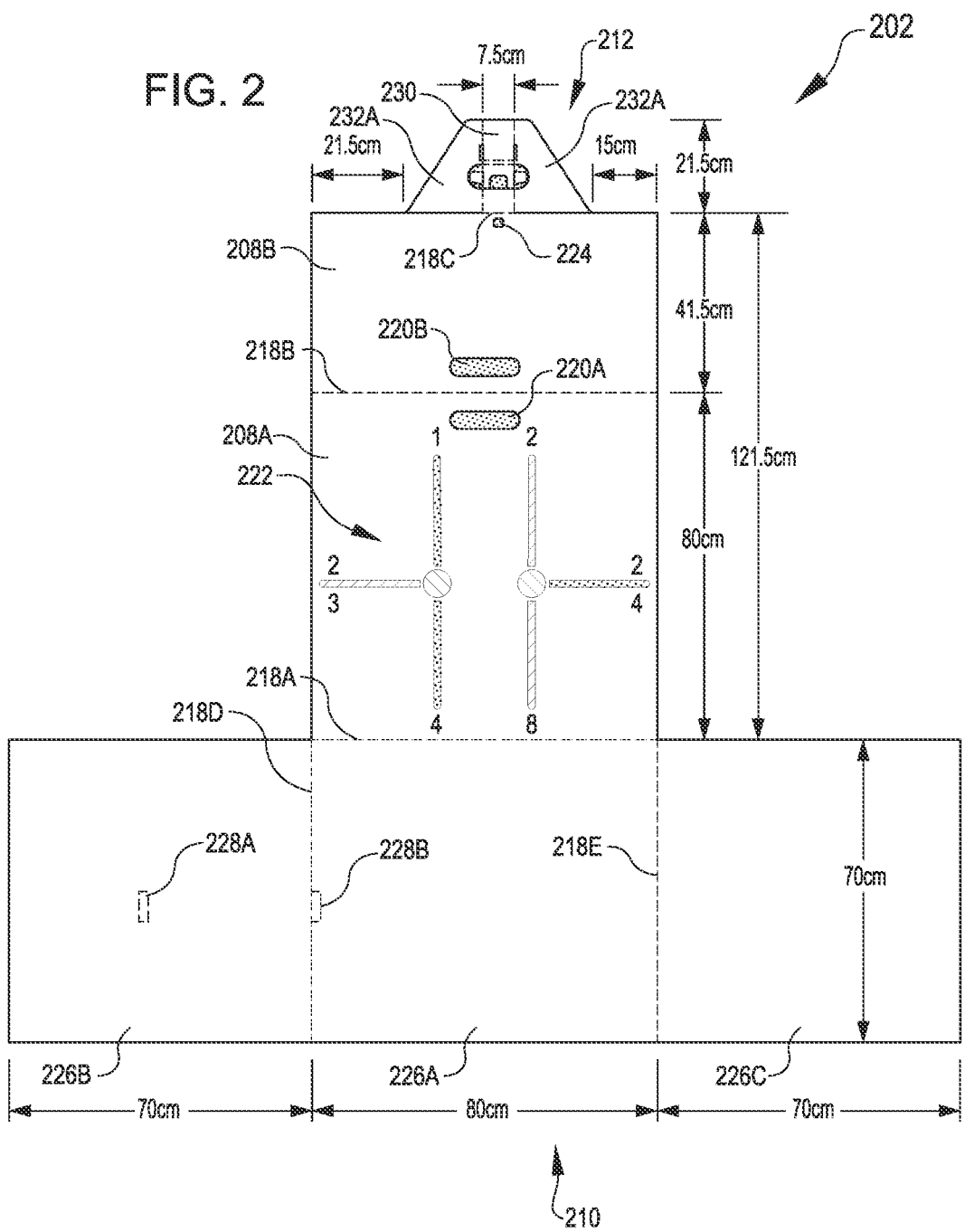
FIG. 2 illustrates a top view of a portable photo studio in a partially assembled state, according to at least one example.
Figure 4:
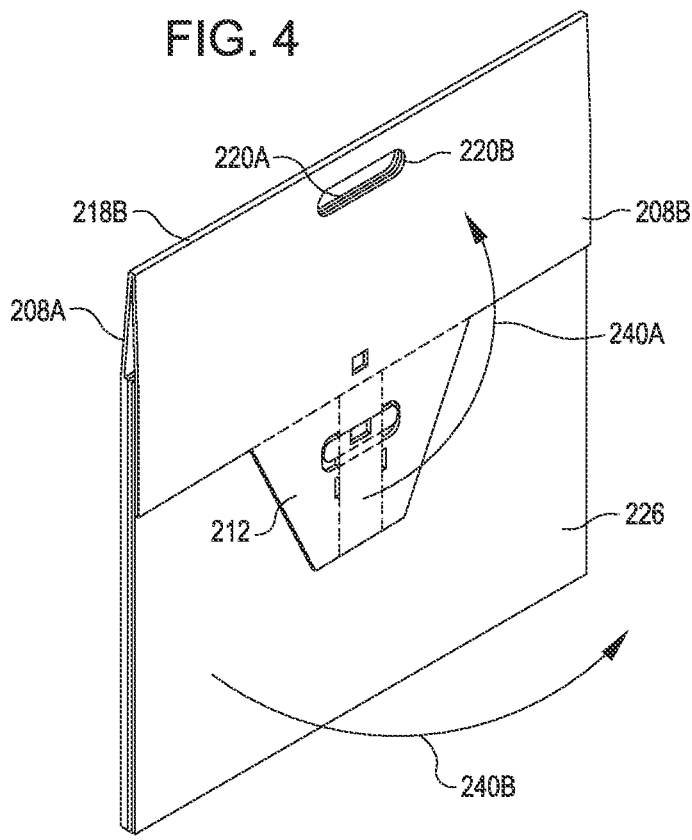
FIG. 4 illustrates a perspective view of a portable photo studio in an unassembled state, according to at least one example.

FIG. 2 illustrates a top view of a portable photo studio 202 in a partially assembled state, according to at least one example. The portable photo studio 202 is an example of the portable photo studio 102. The portable photo studio 202 may take the form as illustrated in FIG. 2 during a setup operation, described with reference to later figures. The portable photo studio 202 may also take the form illustrated in FIG. 2 shortly after manufacturing is complete and before being bundled together, as shown in FIG. 4. For example, multiple portable photo studios 202 may be formed from a single piece of planar material such as corrugated cardboard (e.g., single faced corrugated paper, single wall corrugated paper (double faced), double wall corrugated paper), wood (e.g., plywood, particle board, wood paneling), plastic (acrylic or polymethyl methacrylate (PMMA), polycarbonate (PC), polyethylene (PE), polypropylene (PP), polyethylene terephthalate (PETE or PET), polyvinyl chloride (PVC), acrylonitrile-butadiene-styrene (ABS)), and any other suitable planar material. A die cutting machine or other comparable manufacturing apparatus may be used to cut the shape of the portable photo studio 202 and any interior slots, and to form various hinges between sections of the portable photo studio 202. As part of manufacturing the portable photo studio 202, text, markings, and the like may also be applied to surfaces of the portable photo studio 202 (e.g., using printing, painting, etching, etc.). The text may provide instructions for setting up the portable photo studio 202.

In some examples, the portable photo studio 202 may be formed from multiple separate panels that are joined together using any suitable technique, e.g., adhesive tape, staples, zippers, glue, and the like. For example, the panels of the portable photo studio 202 may be joined together at each of the hinges 218. In particular, the electronics stand 212, including its various parts, the bottom section parts 208B and 208A, and each of the side walls 226A-226C may be formed as separate parts that may be joined together either during manufacturing or during assembly by a user. For example, the portable photo studio 202 may be provided to users with instructions for assembling the various parts together using one or more suitable techniques, such as those described above.

Turning now to the elements of the portable photo studio 202 in more detail, the portable photo studio 202 includes a bottom section 208 (labeled as two parts 208A and 208B), a background section 210, and an electronics stand 212. The bottom section 208 forms the base or bottom of the portable photo studio 202. When in use, the user stands on at least a portion of the bottom section 208.

The bottom section 208 of the portable photo studio 202 includes at least two bottom section parts 208A and 208B. The bottom section part 208A is connected to the background section 210 via a hinge 218A and the bottom section part 208B via a hinge 218B. As described herein, the hinges 218 may refer to pliable joints between two or more panels of the portable photo studio 202. In some examples, the hinges may be formed by a machine that preforms bend lines in a single piece of material to define two panels separated by a hinge. Thus, the hinges 218 may be formed as a continuous portion of the same material or may be formed by connecting to panels together, which may include a part disposed between the two panels (e.g., a flexible plastic or other material that is glued or otherwise adhered to the two parts), or may be formed in any other suitable manner. The bottom section part 208A includes a handle opening 220A for use when transporting the portable photo studio 202. The bottom section part 208A also includes a set of reference indicia 222. The set of reference indicia 222, which will be described in more detail with reference to later figures, is useable by the user to orient her legs into various poses.

When in use, the user will stand on the bottom section part 208A in the area occupied by the reference indicia 222.

The bottom section part 208B is connected to the electronics stand 212 via a hinge 218C. The bottom section part 208B includes a handle opening 220B for use when transporting the portable photo studio 202. As illustrated in FIG. 4, the two handle openings 220A and 220B come together when the portable photo studio 202 is in the unassembled state. The bottom section part 208B also includes a mounting hole 224 for mounting a light source, as described herein with reference to FIG. 10.

The background section 210 includes three side walls 226A, 226B, and 226C, sometimes referred to herein as panels. The bottom section 208 and the background section 210, including the three side walls 226A-226C, may be painted a color that has good photographic characteristics in terms of light absorbance and reflectance. For example, the bottom section 208 and the background section 210 may be painted the same color such as a Pantone® Cool Gray 3U, 5U, or other similar colors. In some examples, the color may have the color values substantially similar to the following: Red Green Blue (197, 197, 197) and Cyan Magenta Yellow Black (19, 14, 13, 0). In some examples, other parts of the portable photo studio 202 may be painted the same or different colors. In some examples, other colors having similar photographic characteristics may be selected.

Figure 5:
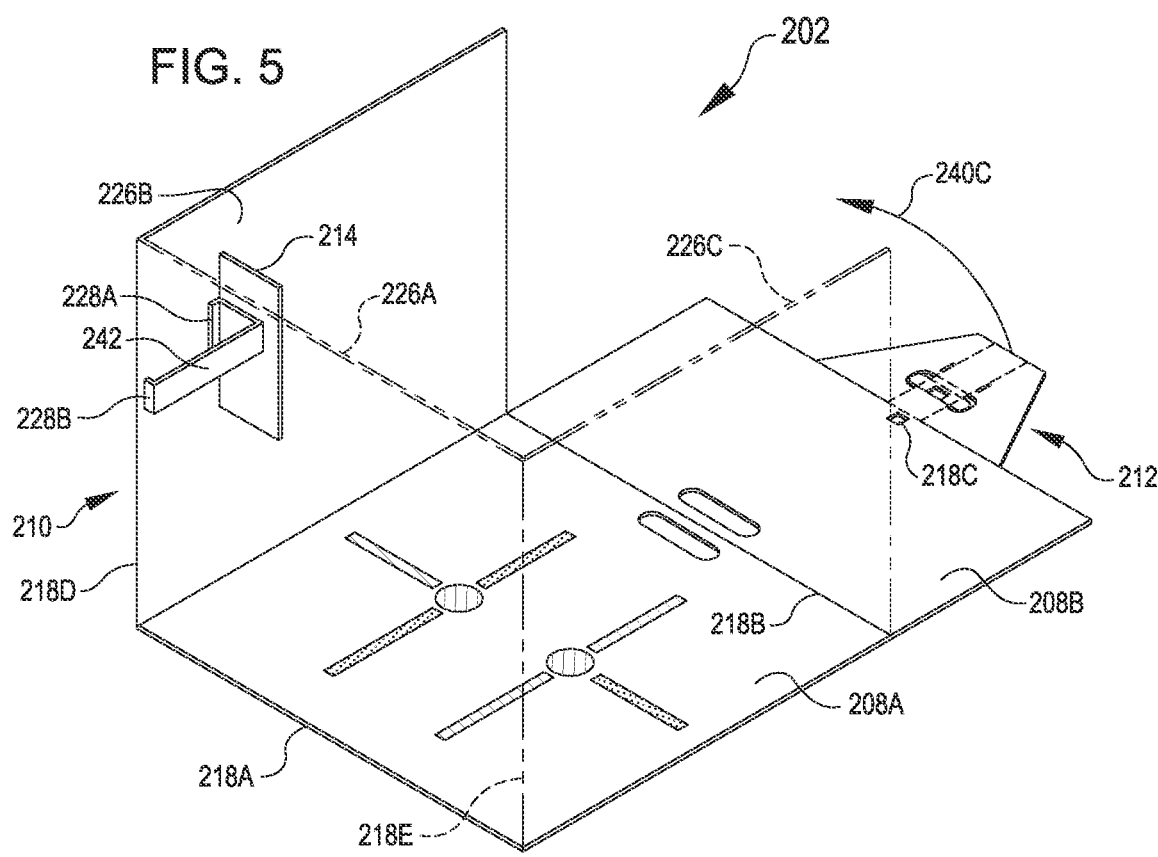
FIG. 5 illustrates a perspective view of the portable photo studio of FIG. 4 in a partially assembled state, according to at least one example.

The side wall 226A, which forms the back of the portable photo studio 202 in the assembled state, is connected to the bottom section part 208A via the hinge 218A and to the other side walls 226B and 226C via hinges 218D and 218E, respectively. The hinge 218A enables the entire background section 210, e.g., all three side walls 226A-226C, to pivot independently with respect to the bottom section part 208A. The hinge 218D enables the side wall 226B to pivot independently with respect to the side wall 226A. The hinge 218E enables the side wall 226C to pivot independently with respect to the side wall 226A. As illustrated in FIGS. 1 and 5, such independent pivoting enables the background section 210 to be folded into a U shape, with the side wall 226A forming a bottom or back of the U shape and the side walls 226B and 226C forming the sides of the U shape. The background section 210 also includes connection points 228A and 228B. As illustrated in FIG. 5, the connection points 228A and 228B may be used to mount a color card (e.g., the color card 114) to the background section 210.

In FIG. 2, example dimensions are included for reference only. Depending on the implementation, the values of the dimensions may be greater than or less than those described. For example, the portable photo studio 202 may be suitable for capturing images of human legs, but if a different part of the anatomy were being imaged, the dimensions may be different (e.g., to image a torso region, the electronics stand may be positioned further from the reference indicia 222 and the side walls 226 may be taller).

Figure 3:
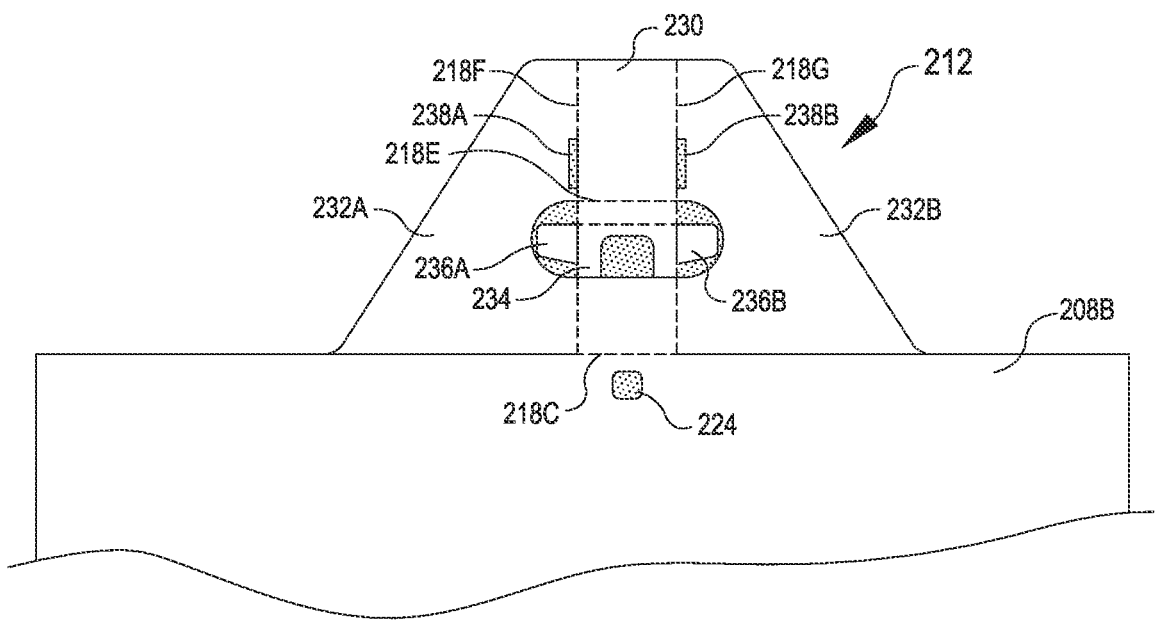
FIG. 3 illustrates a zoomed-in view of an electronics stand of the portable photo studio of FIG. 2, according to at least one example.

FIG. 3 illustrates a zoomed-in view of the electronics stand 212 of the portable photo studio 202, according to at least one example. Generally, the electronics stand 212 is any suitable structure capable of supporting an electronic device. The electronics stand 212 includes a main body 230 and a pair of wings 232A and 232B. The main body 230 is connected to the bottom section part 208B via the hinge 218C. The hinge 218C enables the electronics stand 212 to independently pivot with respect to the bottom section part 208B.

The wings 232A and 232B are connected to the main body 230 via hinges 218F and 218G, respectively. The hinges 218F and 218G enable the wings 232A and 232B to pivot independently with respect to the main body 230. In the assembled state, as illustrated in FIG. the wings 232A and 232B may be pivoted way from the main body 230 to support the electronics stand 212.

Figure 7:
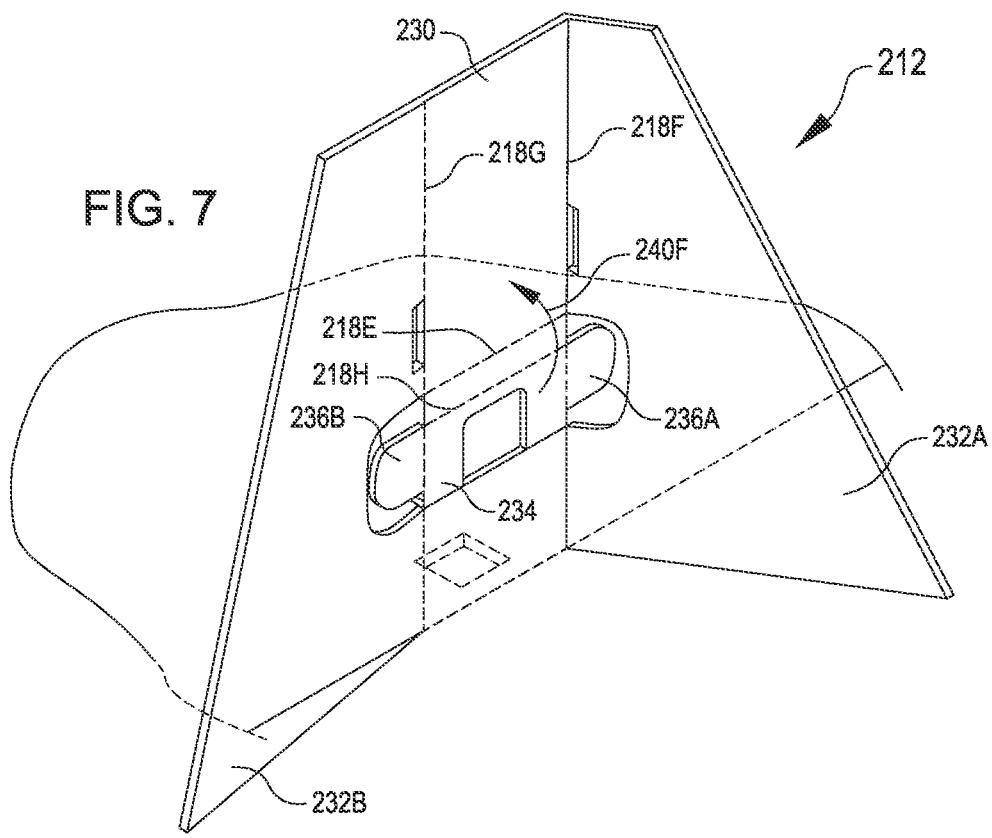
FIG. 7 illustrates a perspective view of the electronics stand of the portable photo studio of FIG. 4 in a partially assembled state, according to at least one example.
Figure 8:
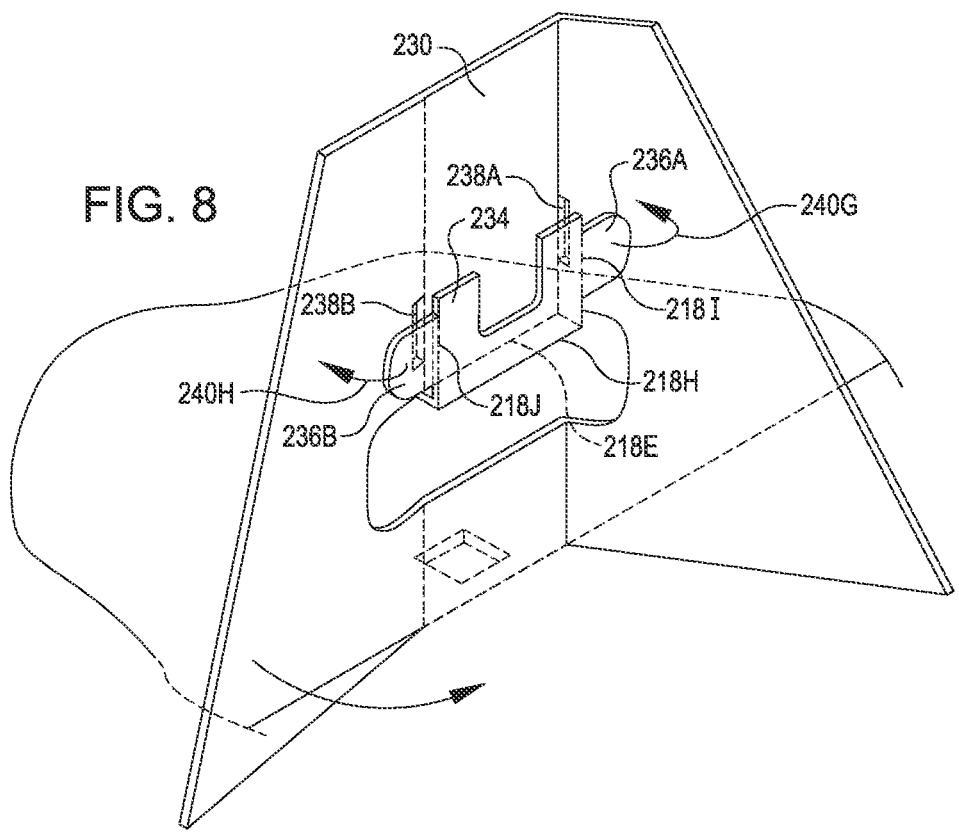
FIG. 8 illustrates a perspective view of the electronics stand of the portable photo studio of FIG. 4 in a partially assembled state, according to at least one example.
Figure 9:
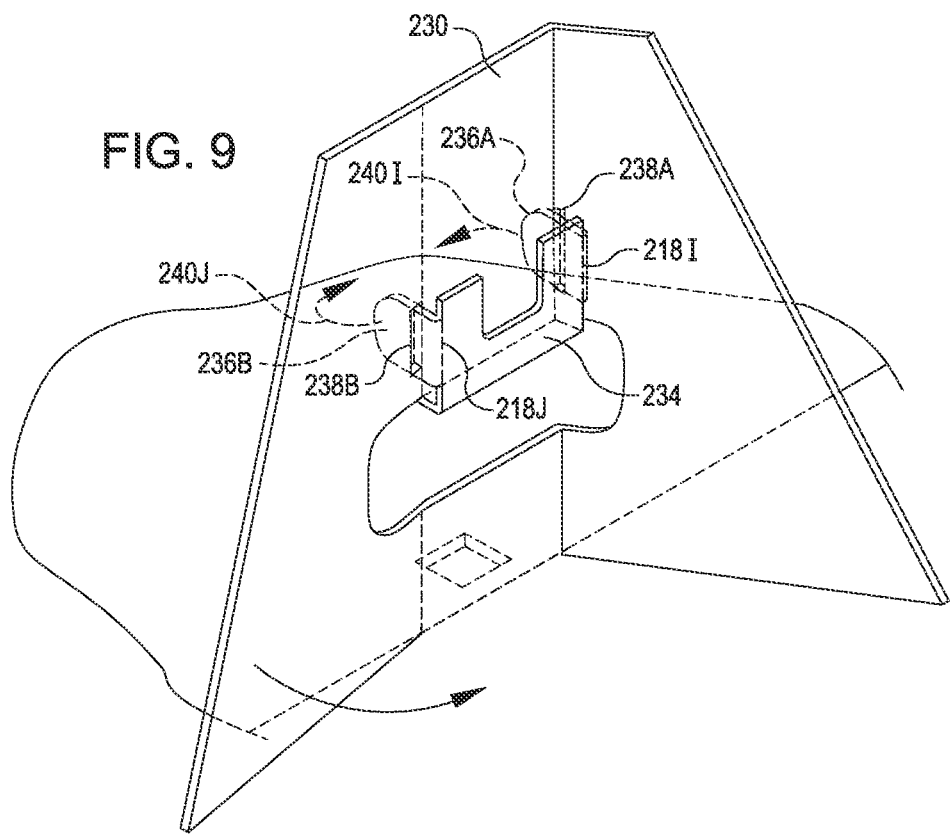
FIG. 9 illustrates a perspective view of the electronics stand of the portable photo studio of FIG. 4 in a partially assembled state, according to at least one example.
Figure 10:
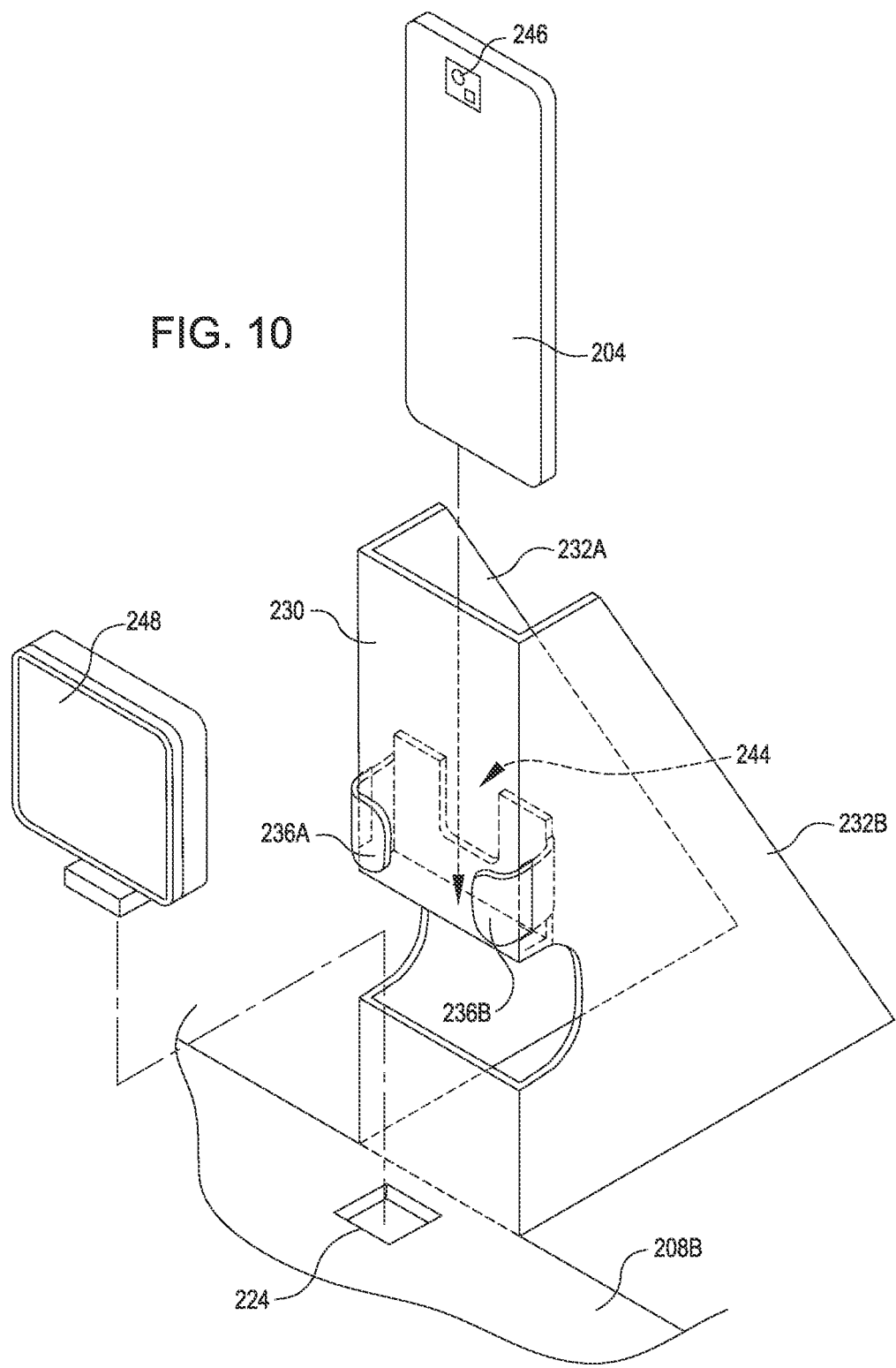
FIG. 10 illustrates a perspective view of the electronics stand of the portable photo studio of FIG. 4 in an assembled state, according to at least one example.

The electronics stand 212 also includes a pocket cutout 234 including tabs 236A and 236B. Generally, as illustrated in FIGS. 7-9, the pocket cutout 234 may be pivoted to create a pocket for receiving and supporting an electronic device (e.g., the electronic device 104). To form the pocket, the pocket cutout 234 including the tabs 236A and 236B are pivoted about 90 degrees about a hinge 218E at which point the tabs 236A and 236B are pivoted about 90 degrees with respect to the pocket cutout 234. Next, the tabs 236A and 236B are inserted into tab slots 238A and 238B and distal ends of the tabs 236A and 236B are bent towards and adhered to the main body 230, as shown in FIG. 10.

While the electronics stand 212 is illustrated as being integrally formed, the electronics stand 212 may, in some examples, include a separate device that is mountable or alignable with the bottom section part 208B and configured to mount and align the electronic device. For example, the electronics device 212 may include a tripod and indicators for aligning the tripod may be applied to the bottom section part 208B, a tripod screw mount in the bottom section part 208B, or any other suitable mounting mechanism that is built into the portable photo studio 202.

FIG. 4 illustrates a perspective view of the portable photo studio 202 in an unassembled state, according to at least one example. In the unassembled state, the portable photo studio 202 may be suitable for transportation. For example, the two handle openings 220A and 220B form a through opening by which a user may grasp the portable photo studio 202. In the unassembled state, parts of the portable photo studio 202 overlap other parts of the portable photo studio 202. For example, the bottom section 208 is bent at the hinge 218B such that the bottom section part 208A overlays a portion of one of the side walls 226 (e.g., the side wall 226B or 226C). In some examples, the bottom section part 208A and/or the electronics stand 212 may be releasably connected to one of the side walls 226 to keep the portable photo studio 202 bundled together. For example, the electronics stand 212 may include a tab at a distal end that inserts into a slit in the side wall 226.

FIG. 5 illustrates a perspective view of the portable photo studio 202 in a partially assembled state, according to at least one example. For example, the portable photo studio 202 illustrated in FIG. 4 has begun to be unfolded, as illustrated in FIG. 5. To begin, a user may lay the portable photo studio 202 down flat on its backside on the floor or other surface, e.g., with the side illustrated in FIG. 4 (including the electronics stand 212) facing up. Next, the user may rotate the electronics stand 212 and the bottom section part 208A via the hinge 218B, as illustrated by arrow 240A in FIG. 4, at least until the bottom section part 208A and the electronics stand 212 are lying flat, as illustrated in FIG. 5. Next, the user may rotate the background section 210 via the hinge 218A, as illustrated by arrow 240B in FIG. 4, at least until the side wall 226A is upright and about perpendicular to the bottom section part 208A. As part of this step or as subsequent steps, the user may rotate the side walls 226B and 226C outward and away from the side wall 226C via the hinges 218D and 218C respectively at least until, as illustrated in FIG. 5, bottom edges of the side walls 226B and 226C are aligned with side edges of the bottom section 208. In this manner, the background section 210 forms a U shape. As the side wall 226B is rotated outward and away from the side wall 226A, a color card 214 is presented. The color card 214 is mounted to a popup part 242, ends of which are connected to the connection points 228A and 228B. Because the popup part 242 is connected to the two side walls 226A and 226B, as the side wall 226B is rotated, the popup part 242 is pulled open to reveal the color card 214. In some examples, the color card 214 is connected to only one of the side walls 226. In some examples, references colors of the color card 114 may be printed, painted, or otherwise secured to the popup part 242.

FIGS. 6-10 illustrates perspective views of the electronics stand 212 of the portable photo studio 202 at various states of assembly, according to various examples. Beginning with the state of the electronics stand 212 illustrated in FIG. 5 and to achieve the state illustrated in FIG. 6, the user may rotate the electronics stand 212 via the hinge 218C, as illustrated by arrow 240C in FIG. 5, at least until the electronics stand 212 is upright and about perpendicular to the bottom section part 208B.

Figure 6:
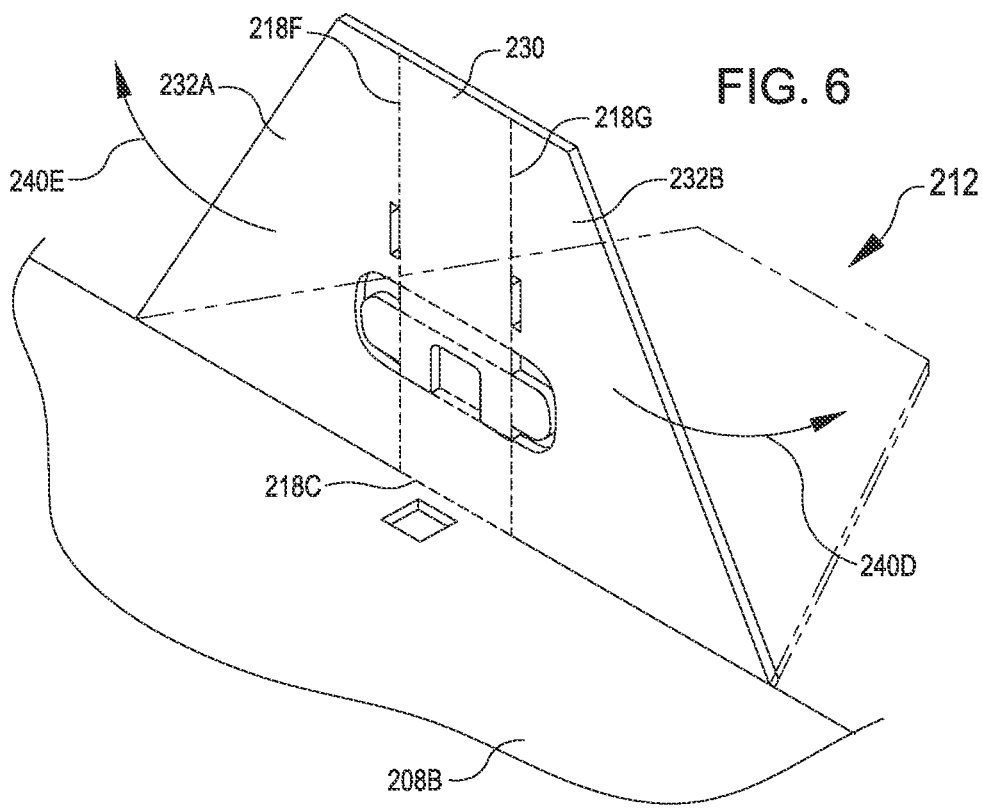
FIG. 6 illustrates a perspective view of an electronics stand of the portable photo studio of FIG. 4 in a partially assembled state, according to at least one example.

Beginning with the state of the electronics stand 212 illustrated in FIG. 6 and to achieve the state illustrated in FIG. 7 (and also in FIG. 10), the user may rotate the wings 232A and 232B, via the hinges 218F and 218G respectively, as illustrated by arrows 240D and 240E in FIG. 6, outward and away from the bottom section part 208B at least until the wings 232A and 232B are about perpendicular to the main body 230. In FIG. 7, the wing 232B has not been entirely rotated about the hinge 218G in order to accommodate the assembly of an electronics pocket 244 (see FIG. 10), which is formed form the pocket cutout 234 and the tabs 236A and 236B.

Beginning with the state of the electronics stand 212 illustrated in FIG. 7 and to achieve the state illustrated in FIG. 8, the user may rotate the pocket cutout 234 including the tabs 236A and 236B, via the hinge 218E, as illustrated by arrow 240F in FIG. 7, 180 degrees at least until the pocket cutout 234 is parallel to the main body 230. As the pocket cutout 234 is rotated a second rotation is performed about hinge 218H. This rotation begins to form the electronics pocket 244.

Beginning with the state of the electronics stand 212 illustrated in FIG. 8 and to achieve the state illustrated in FIG. 9, the user may rotate the tabs 236A and 236B, via the hinges 218I and 218J respectively, as illustrated by arrows 240G and 240H in FIG. 8, about 90 degrees and insert the tabs 236A and 236B through the corresponding tab slots 238A and 238B.

Beginning with the state of the electronics stand 212 illustrated in FIG. 9 and to achieve the state illustrated in FIG. 10, the user may bend the tabs 236A and 236B again as illustrated by arrows 240I and 240J in FIG. 9, about 90 degrees at least until the distal ends of the tabs 236A and 236B contact the surface of the main body 230. The distal ends of the tabs 236A and 236B may be glued or otherwise adhered to the surface of the main body 230 to rigidly define the electronics pocket 244 on the opposite side of the main body 230. As illustrated in FIG. 10, the electronics pocket 244 is sized and configured to receive an electronic device 204 (e.g., the electronic device 104). In some examples, the electronic device 204 may be held in the electronics pocket 244 using an interference fit, a set of snaps, or in any other suitable manner.

As illustrated in FIG. 10, the electronic device 204 includes a camera 246. The electronic device 204 is mounted into the electronics pocket 244 with the camera 246 facing the background section 210 (e.g., an interior volume of the U shape). In this manner, the camera 246 can be used to take images of a user standing on the bottom section 208 within the U shape. The electronic device 204 is a smartphone and the camera 246 is a back-facing camera, e.g., on the backside of the smartphone. In some examples, the camera 246 may be a front-facing camera of the smartphone, e.g., on the same side as a screen of the electronic device 204. In this example, the electronics pocket 244 may be reconfigured such that the screen of the electronic device 204 and the camera 246 may be visible to the user. This may enable the application running on the electronic device 204 to output visual instructions (e.g., text, images, videos, and the like) via the screen that can be viewed by the user standing on the bottom section 208. In some examples, the instructions, whether visual or otherwise, may be displayed on a different electronic device (e.g., a tablet device) that is viewable by the user.

As illustrated in FIG. 10, a light source 248 is mountable within the mounting hole 224. The light source 248 may be battery-powered and, in some examples, may be adjustable. For example, the brightness of the light source 248 may be adjusted to account for ambient conditions in which the portable photo studio 202 is installed. In some examples, the electronic device 204 may include a light sensor to measure ambient light, and, based on such measurements, the electronic device 204 may determine whether and by how much to adjust the light source 248.

Figure 11:
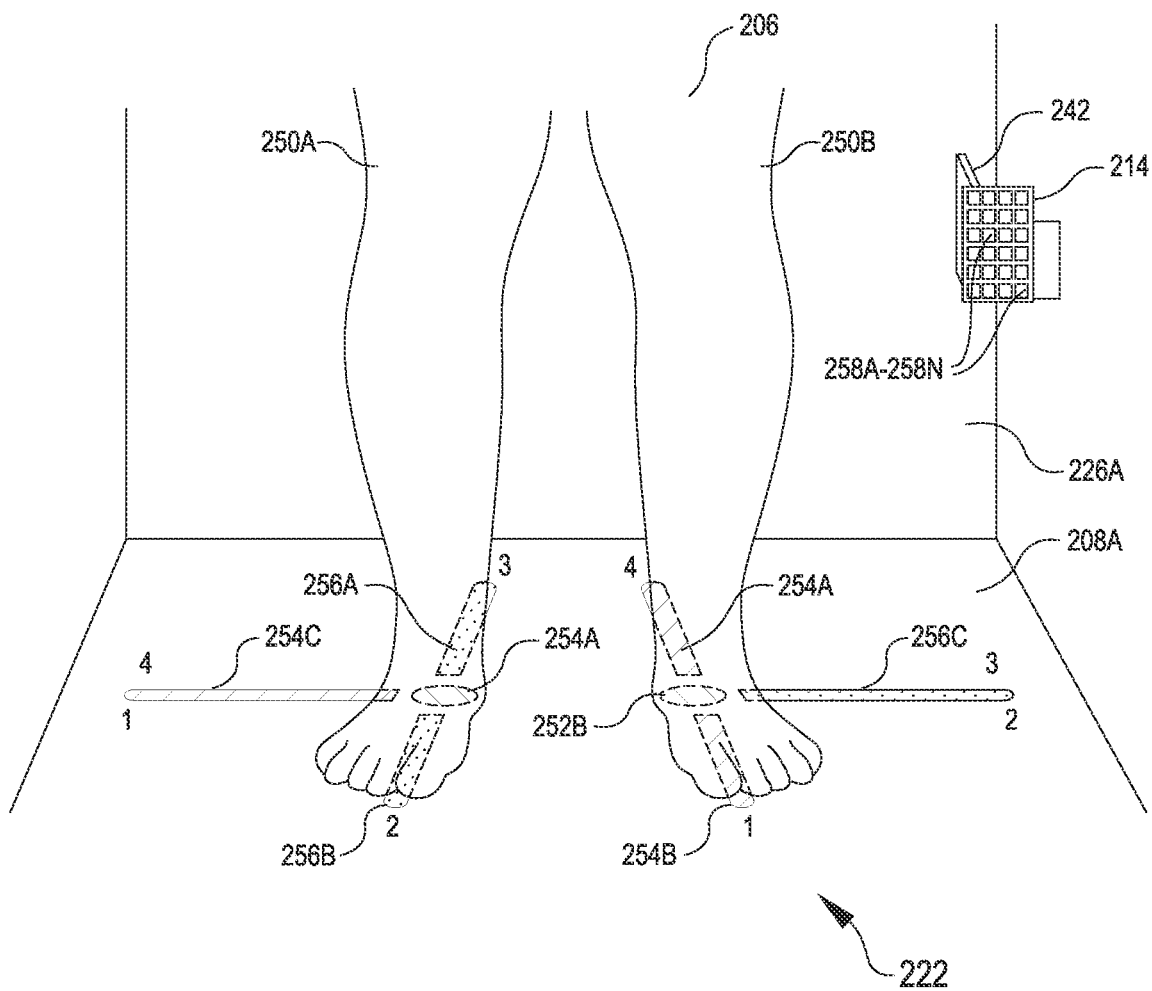
FIG. 11 illustrates a front view of a portable photo studio including a pair of legs in an orientation, according to at least one example.

FIG. 11 illustrates a front view of the portable photo studio 202 including a pair of legs 250 of a user 206 in an orientation, according to at least one example. The pair of legs 250, which include a first leg 250A and a second leg 250B, are in a neutral orientation in FIG. 11. For example, after the user 206 has set up the portable photo studio 202, as described with reference to FIGS. 4-10, the user 206 may participate in an image capture session, which may be conducted by the electronic device 204 and is described in additional detail with reference to FIGS. 12-15.

FIG. 11 also illustrates the reference indicia 222 and the color card 214 in additional detail. The reference indicia 222 include heel indicia 252A and 252B, a first type of orientation indicia 254A-254C (e.g., identified by a first color such as red), and a second type of orientation indicia 256A-256B (e.g., identified by a second color such as blue). In some examples, the reference indicia 222 may be divided into two reference indicium groups. A first group includes the heel indicium 252A, the orientation indicia 254A and 254B, and the orientation indicium 256C. A second group includes the heel indicium 252B, the orientation indicia 256A and 256B, and the orientation indicium 254C. In some examples, the instructions for orienting the pair of legs 250 may be given with respect to the different reference indicia 222. To begin, the user 206 may place her heels on the heel indicia 252A and 252B. In some examples, the heels may remain on the heel indicia 252A and 252B during the entirety of the image capture session. The sets of numbers 1-4 correspond to different orientations and are included for reference. For example, an instruction may reference the numbers, the particular indicia, and/or a degrees of rotation to orient the pair of legs 250.

The color card 214, as illustrated, is mounted perpendicular to the side walls 226B and 226C and parallel to the side wall 226A. The length of the popup part 242 is selected to place position the color card 214 at a depth that is about equal to a depth of the heel indicia 252A and 252B. The camera 246 is spaced apart from the heel indicia 252A to ensure that the pair of legs 250 will be in focus when images are captured of the pair of legs 250. Because the color card 214 is in about the same plane as the pair of legs 250, the color card 214 will also be in focus in the images. The height of the mounting location of the color card 214 (e.g., between the bottom section part 208A and the midpoint of the color card 214) is selected such that the color card 214 is about level with the middle of the pair of legs 250 (e.g., at or about an average knee height).

The color card 214 includes a plurality of reference colors 258A-258N. The reference colors 258 are used to calibrate the camera 246 and to identify the correct skin tone of the pair of legs 250. In some examples, the color card 214 may be a ColorChecker Classic target array manufactured by X-rite and includes twenty-four reference colors. In some examples, the references colors 258A-258N of the color card 114 may be printed, painted, or otherwise secured to the popup part 242, the background section 110, or the like.

Figure 12:
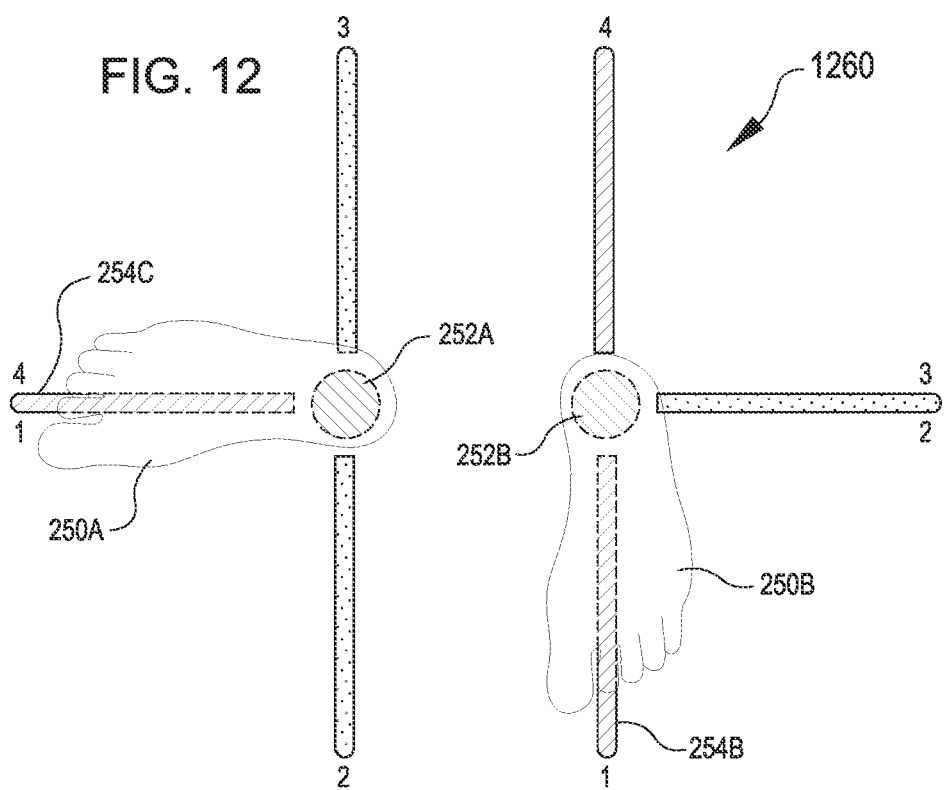
FIG. 12 illustrates a top view of a portable photo studio including a pair of legs in an orientation, according to at least one example.

FIGS. 12-15 illustrate top views of the portable photo studio 202 including the pair of leg 250 in various orientations, according to various examples. FIGS. 12-15 illustrate four different orientations for the pair of legs 250. In particular, FIG. 12 illustrates a first orientation 1260 for imaging the pair of legs 250. In the first orientation 1260, the heels are placed on the heel indicia 252A and 252B, the left leg 250B is aligned with the first type of orientation indicium 254B (e.g., toes of the left leg 250B are pointing towards the camera 246), and the right leg is aligned with the first type of orientation indicium 254C (e.g., the right leg 250A is rotated degrees from the neutral orientation). At this point, the camera 246 may capture an image of the pair of legs 250 in the first orientation 1260. For example, a voice instruction from the electronic device 204 may first give the instructions for the user to put her legs 250 into the first orientation 1260 and afterwards the voice instruction may be a countdown (e.g., 5 . . . 4 . . . 3 . . . 2 . . . 1) before capturing the image. As described elsewhere herein, the countdown may also be visual such as a blinking light, a screen that includes a countdown, etc. In some examples, the user may use a voice command to instruct the camera to take the image, to retake images, to stop and/or begin an image capture session, and the like. For example, the electronic device 204 may include a voice assistant.

Figure 13:
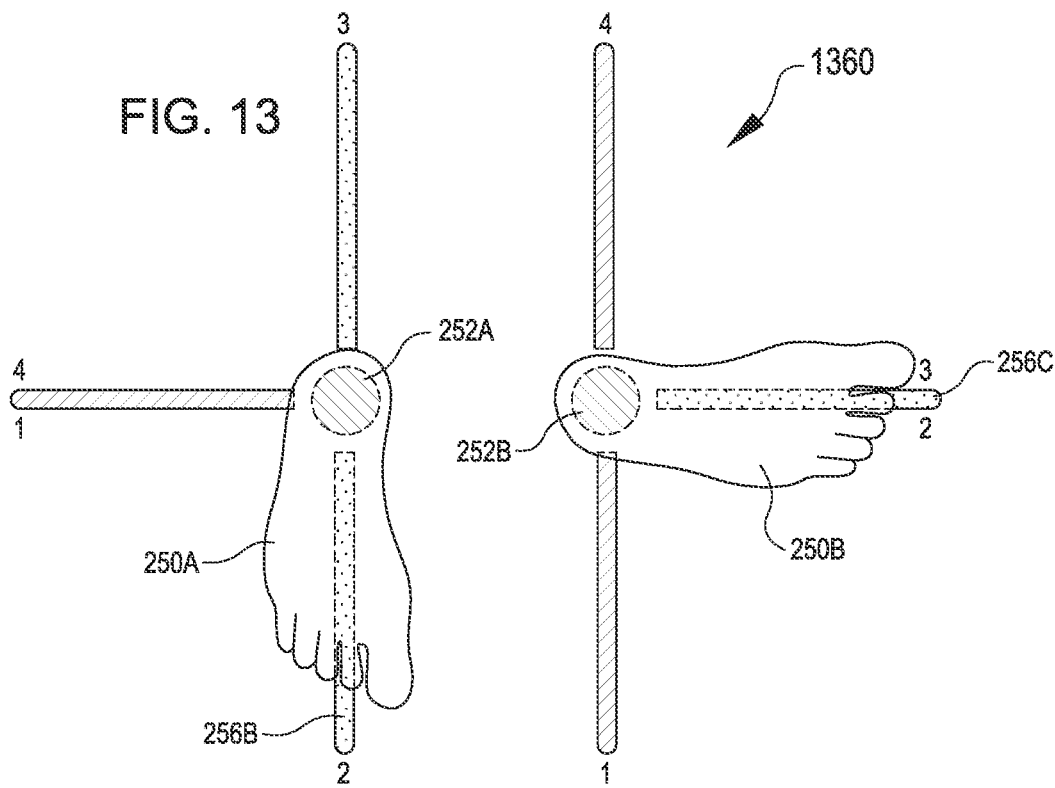
FIG. 13 illustrates a top view of a portable photo studio including a pair of legs in an orientation, according to at least one example.

After one or more images have been captured in the first orientation 1260, the user 206 may be instructed to orient the pair of legs 250 into a second orientation 1360, as illustrated by FIG. 13. In the second orientation 1360, the heels are placed on the heel indicia 252A and 252B, the left leg 250B is aligned with the second type of orientation indicium 256C (e.g., the left leg 250B is rotated 90 degrees from the neutral position), and the right leg 250A is aligned with the second type of orientation indicium 256B (e.g., toes of the right leg 250A are pointing towards the camera 246). At this point, the camera 246 may capture an image of the pair of legs 250 in the second orientation 1360. For example, a voice instruction from the electronic device 204 may first give the instructions for the user to put her legs 250 into the second orientation 1360 and afterwards the voice instruction may be a countdown (e.g., 5 . . . 4 . . . 3 . . . 2 . . . 1) before capturing the image. As described elsewhere herein, the countdown may also be visual such as a blinking light, a screen that includes a countdown, etc.

Figure 14:
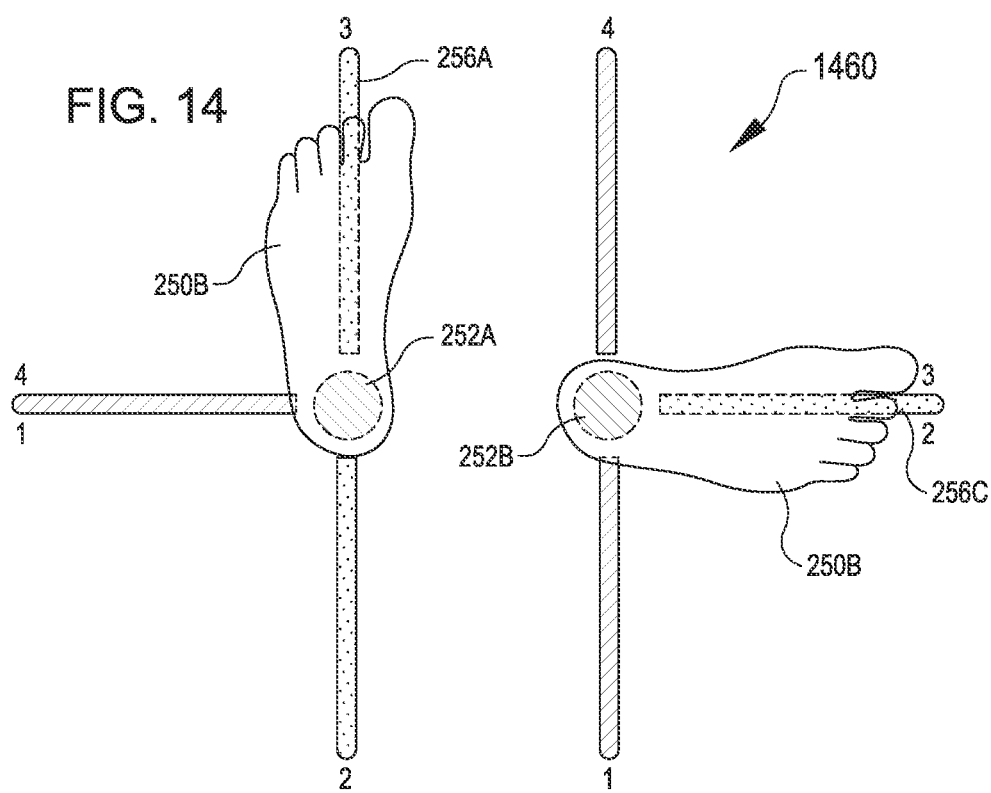
FIG. 14 illustrates a top view of a portable photo studio including a pair of legs in an orientation, according to at least one example.

After one or more images have been captured in the second orientation 1360, the user 206 may be instructed to orient the pair of legs 250 into a third orientation 1460, as illustrated by FIG. 14. As part of moving to the third orientation 1460, the user 206 has rotated 180 degrees from the neutral position (e.g., the backs of the user's legs are now facing the camera). In the third orientation 1460, the heels are placed on the heel indicia 252A and 252B, the left leg 250B is aligned with the second type of orientation indicium 256A (e.g., toes of the left leg 250B are pointing away from the camera 246 and towards the side wall 226A), and the right leg 250A is aligned with the second type of orientation indicium 256C (e.g., the right leg 250A is rotated 90 degrees to the right). At this point, the camera 246 may capture an image of the pair of legs 250 in the third orientation 1460. For example, a voice instruction from the electronic device 204 may first give the instructions for the user to put her legs 250 into the third orientation 1460 and afterwards the voice instruction may do a countdown (e.g., 5 . . . 4 . . . 3 . . . 2 . . . 1) before capturing the image. As described elsewhere herein, the countdown may also be visual such as a blinking light, a screen that includes a countdown, etc.

Figure 15:
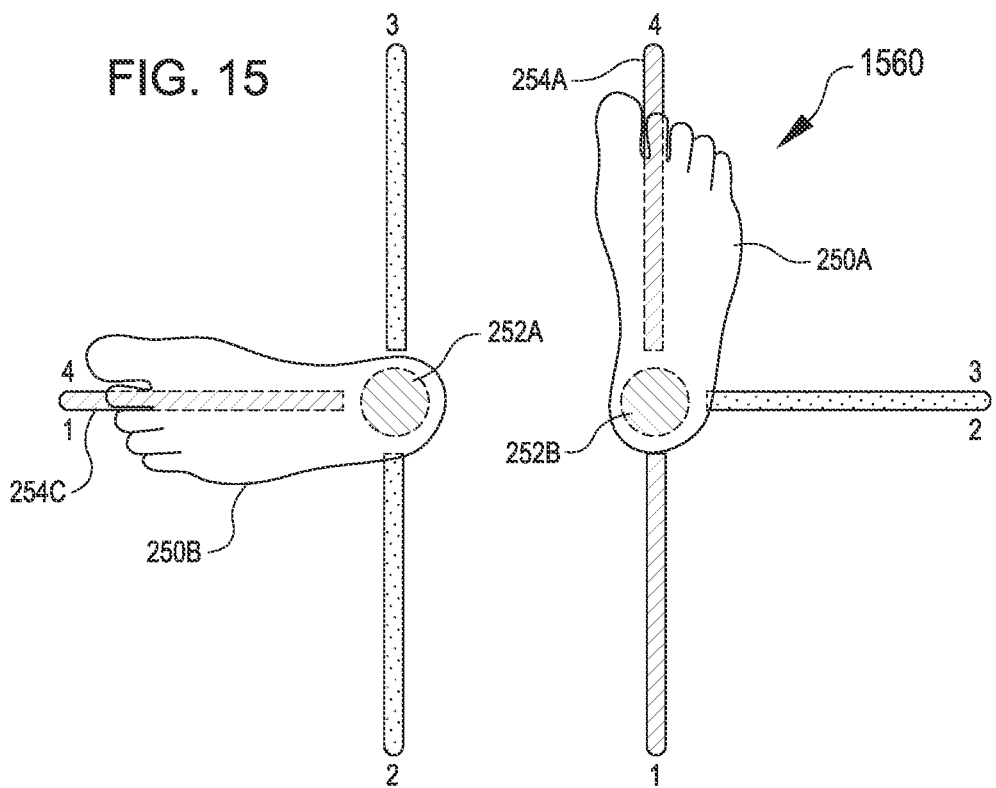
FIG. 15 illustrates a top view of a portable photo studio including a pair of legs in an orientation, according to at least one example.

After one or more images have been captured in the third orientation 1460, the user 206 may be instructed to orient her legs 250 into a fourth orientation 1560, as illustrated by FIG. 15. Like in the third orientation 1460, the user 206 has rotated 180 degrees from the neutral position before moving into the fourth orientation 1560. In the fourth orientation 1560, the heels are placed on the heel indicia 252A and 252B, the left leg 250B is aligned with the first type of orientation indicium 254C (e.g., the left leg 250B is rotated 90 degrees to the left), and the right leg 250A is aligned with the first type of orientation indicium 254A (e.g., toes of the right leg 250A are pointing away from the camera 246 and towards the side wall 2226A). At this point, the camera 246 may capture an image of the pair of legs 250 in the fourth orientation 1560. For example, a voice instruction from the electronic device 204 may first give the instructions for the user to put her legs 250 into the fourth orientation 1560 and afterwards the voice instruction may do a countdown (e.g., 5 . . . 4 . . . 3 . . . 2 . . . 1) before capturing the image. As described elsewhere herein, the countdown may also be visual such as a blinking light, a screen that includes a countdown, etc.

Figure 16:
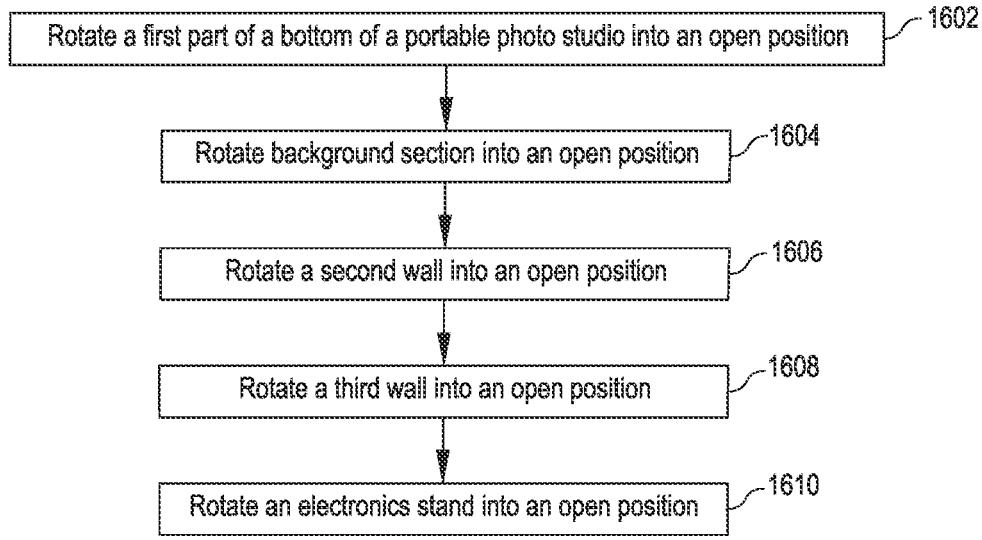
FIG. 16 illustrates a flow chart showing a process for setting up a portable photo studio, according to at least one example.

FIG. 16 illustrates a flow chart showing a process 1600 for setting up the portable photo studio 202, according to at least one example. The process 1600 may be performed by the user 206, another user such as a clinician assigned to help the user 206, and any other suitable user. The instructions for performing aspects of the process 1600 may be printed on the portable photo studio 202 itself, included in a corresponding computer application, and/or printed in an instruction booklet.

The process 1600 begins at block 1602 by rotating a first part of a bottom of the portable photo studio into an open position. Rotating the first part may include rotating at a first hinge of the portable photo studio. The portable photo studio is an example of the portable photo studio 202 which includes the bottom, a background section including a first wall, a second wall, and a third wall, and an electronics stand. The first hinge may be integrally formed between the first part of the bottom and the second part of the bottom. If the first hinge is not integrally formed between the first part of the bottom and the part of the bottom, the block 1602 may include forming the first hinge by coupling together the first part of the bottom and the second part of the bottom and moving the parts in the open position.

At block 1604, the process 1600 includes rotating the background section into an open position. Rotating the background section may include rotating at a second hinge of the portable photo studio. The second hinge may be integrally formed between a second part of the bottom and the first wall of the background section. If the second hinge is not integrally formed between the second part of the bottom and the first wall, the block 1604 may include forming the second hinge by coupling together the second part of the bottom and the first wall and moving the background section into the open position.

At block 1606, the process 1600 includes rotating the second wall into an open position. Rotating the second wall may include rotating at a third hinge of the portable photo studio. The third hinge may be integrally formed between the first wall and the second wall. In some examples, the portable photo studio may also include a color card that is connected to at least one of the first wall or the second wall. In this example, rotating the second wall may reveal the color card. If the third hinge is not integrally formed between the first wall and the second wall, the block 1606 may include forming the third hinge by coupling the first wall and the second wall and moving the second wall into the open position.

At block 1608, the process 1600 includes rotating the third wall into an open position. Rotating the third wall may include rotating at a fourth hinge of the portable photo studio. The fourth hinge may be integrally formed between the first wall and the third wall. If the fourth hinge is not integrally formed between the first wall and the third wall, the block 1608 may include forming the fourth hinge by coupling the first wall and the third wall and moving the third wall into the open position.

At block 1610, the process 1600 includes rotating the electronics stand into an open position. Rotating the electronics stand may include rotating at a fifth hinge of the portable photo studio. The fifth hinge may be integrally formed between the first part of the bottom and the electronics stand. In the open positions, the first wall, the second wall, and the third wall may form a U shape, with the electronics stand opposing the U shape. In some examples, a first edge of the second side wall and a second edge of the third side wall may physically contact the bottom when the walls define the U shape. If the fifth hinge is not integrally formed between the electronics stand and the first part of the bottom, the block 1610 may include forming the fifth hinge by coupling the electronics stand and the first part of the bottom and moving the electronics stand into the open position.

In some examples, the process 1600 may further include rotating, at a sixth hinge, a first wing section of electronics stand into an open position, and rotating, at a seventh hinge, a second wing section of the electronics stand into an open position. The sixth hinge and seventh hinge may be integrally formed. For example, the sixth hinge may be integrally formed between the first wing section and a main body section of the electronics stand, and the seventh hinge may be integrally formed between the second wing section and the main body section. If the sixth and seventh hinges are not integrally formed between the first wing section and the second wing section and the main body section, the process 1600 may further include forming the sixth and seventh hinges by coupling the respective wing sections to the main body section and aligning the respective wing sections into the open positions.

In some examples, the process 1600 may further include, after rotating the electronics stand into the open position at the block 1610, mounting an electronic device in the electronics stand. In this example, the electronics stand may support the electronic device in a substantially perpendicular orientation with respect to the bottom.

In some examples, the process 1600 may further include mounting an auxiliary light to the bottom at a position that is adjacent to the electronics stand. The auxiliary light may be oriented towards the background section.

Figure 17:
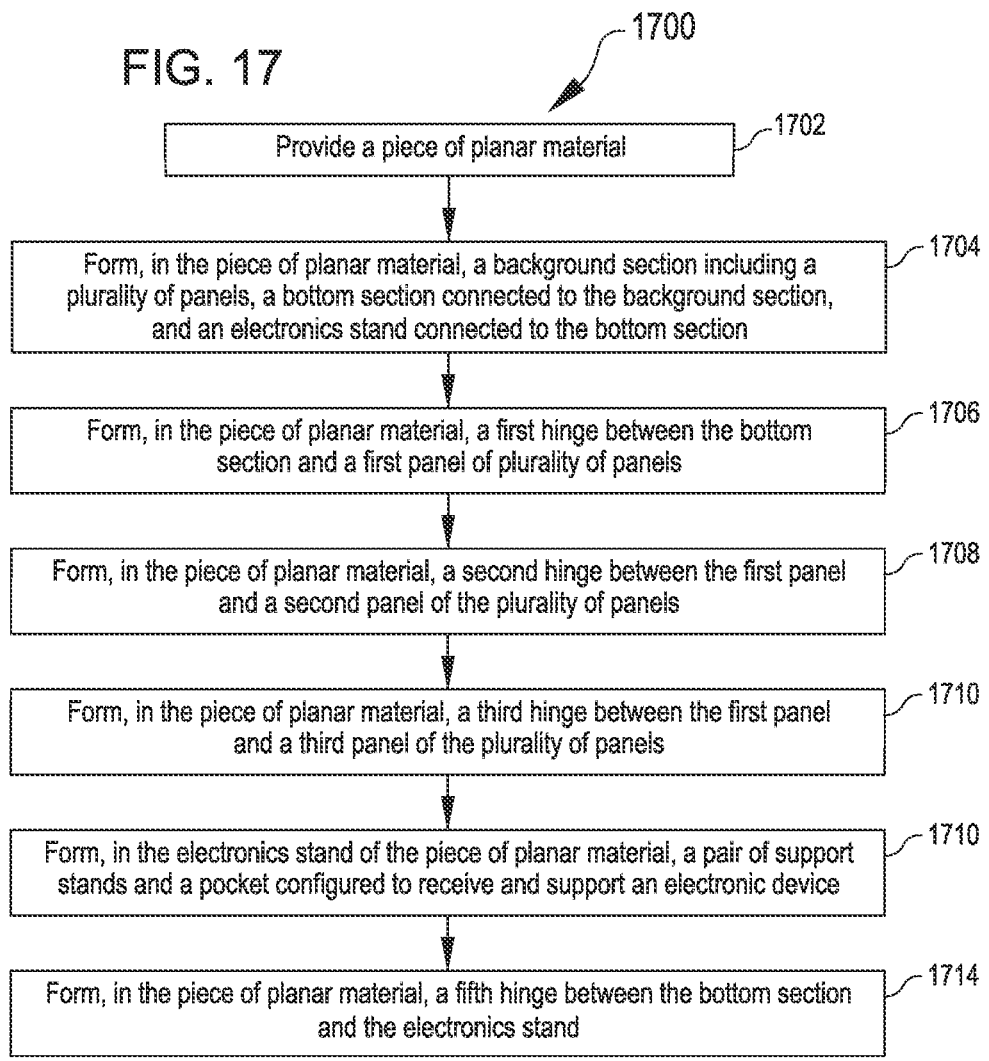
FIG. 17 illustrates a flow chart showing a process for forming a portable photo studio, according to at least one example.

FIG. 17 illustrates a flow chart showing a process 1700 for forming a portable photo studio (e.g., the portable photo studio 202), according to at least one example. The process 1700 may be performed by a forming machine or other producing apparatus managed by a manufacturer, producer, or entity capable of forming the portable photo studio. This example will be discussed with respect to the example photo studio system shown in FIGS. 1 and 2 but may be used with any suitable photo studio system according to this disclosure.

The process 1700 begins at block 1702 by providing a piece of planar material. At block 1704, the process 1700 includes forming, in the piece of planar material, a background section including a plurality of panels, a bottom section connected to the background section, and an electronics stand connected to the bottom section. The planar material may be corrugated cardboard or any other suitable material described herein. The block 1704 may include cutting the piece of planar material to define the bottom section, the plurality of panels, and the electronics stand. At block 1706, the process 1700 includes forming, in the piece of planar material, a first hinge between the bottom section and a first panel of the plurality of panels. At block 1708, the process 1700 includes forming, in the piece of planar material, a second hinge between the first panel and a second panel of the plurality of panels. At block 1710, the process 1700 includes forming, in the piece of planar material, a third hinge between the first panel and a third panel of the plurality of panels. At block 1712, the process 1700 includes forming, in the electronics stand of the piece of planar material, a pair of support stands and a pocket configured to receive and support an electronic device. Forming the pocket at the block 1712 may include cutting a pocket-forming section from the electronics stand that includes a body and a pair of tabs connected to the body, folding the pocket-forming section at a hinge formed between the body and the electronics stand, and connecting the tabs to the electronics stand. At 1714, the process 1700 includes forming, in the piece of planar material, a fifth hinge between the bottom section and the electronics stand.

In some examples, forming any of the hinges, as described herein, may include forming creases at bend lines in the piece of planar material by pressing, rolling, or the like. Forming any of the hinges may also include creating perforations at bend lines in the piece of planar material by pressing, rolling, cutting, or the like. Forming any of the hinges may also include precutting one side of the planar material at bend lines on the exterior side of the hinges by slitting, cutting, sawing, or the like. Forming any of the hinges may also include coupling two separate pieces of material at bend lines by gluing the separate pieces together, zipping the separate pieces together, stapling the separate pieces together, snapping the separate pieces together, taping the separate pieces together, and the like.

In some examples, the process 1700 may further include connecting a color card to at least one of the first panel or the second panel. In some examples, the process 1700 may further include forming one or more elongate openings in the bottom section at a position between the fifth hinge and the first hinge. The elongate openings may function as handles for carrying the portable photo studio. In some examples, the process 1700 may further include applying a plurality of reference indicia to the bottom section. In some examples, the process 1700 may further include painting at least one side of each of the bottom section, the first panel, the second panel, and the third panel the same color. In some examples, the same color is a Pantone® Cool Gray color.

In some examples, the process 1700 may further include folding each of the first panel, the second panel, and the third panel at least until each of the first panel, the second panel, and the third panel overlap a first part of the bottom section; folding the electronics stand at least until the electronics stand overlaps a second part of the bottom section; and folding the second part of the bottom section at least until the second part overlaps the first part of the bottom section.

Figure 18:
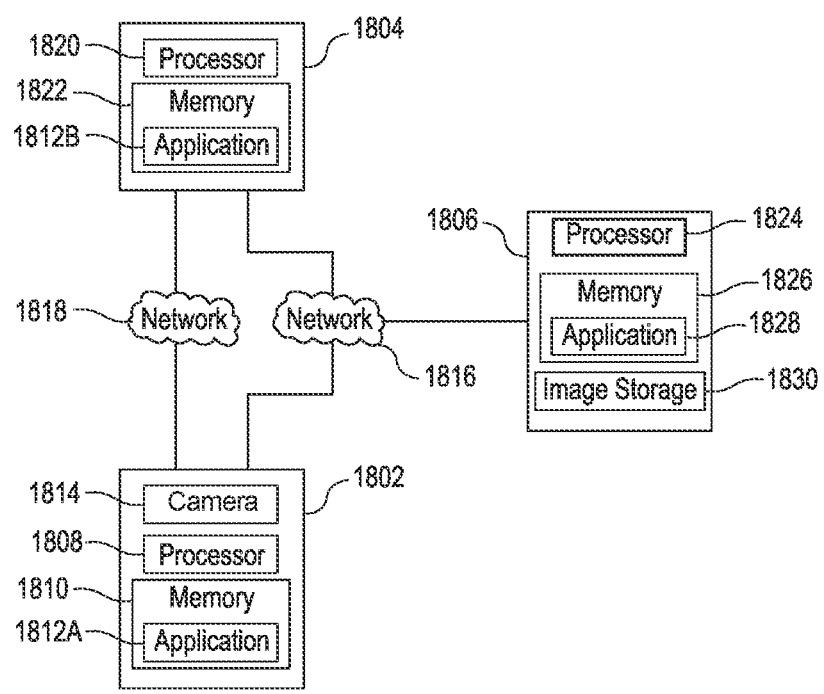
FIG. 18 illustrates an example architecture for interacting with a portable photo studio system, according to at least one example.

FIG. 18 illustrates an example architecture 1800 for interacting with a portable photo studio system, according to at least one example. The architecture 1800 includes a first electronic device 1802, a second electronic device 1804, and a computer system 1806. The first electronic device is an example of the electronic device 104. The second electronic device 1804 is an example of the personal electronic device 116. The first electronic device 1802 and the second electronic device 1804 may be any suitable electronic user device such as a smartphone, tablet, laptop computer, a camera such as a digital single-lens reflex (DSLR) camera with a rotatable screen, and the like.

The first electronic device 1802, the second electronic device 1804, and the computer system 1806 may communicate via one or more networks 1816. The network 1816 can include any appropriate network, including an intranet, the Internet, a cellular network, a local area network, or any other such network or combination thereof. Components used for such a system can depend at least in part upon the type of network and/or environment selected. Protocols and components for communicating via such a network are well known and will not be discussed herein in detail. Communication over the network can be enabled by wired or wireless connections and combinations thereof. For example, the network 1816 may include the Internet, as the environment includes the computer system 1806 receiving and sending requests, although for other networks an alternative device serving a similar purpose could be used as would be apparent to one of ordinary skill in the art.

The first electronic device 1802 and the second electronic device 1804 may communicate via the network 1816 and/or network 1818. The network 1818 may be a local network by which the electronic devices 1802 and 1804 communicate. For example, the network 1818 may be a low-power, short distance wireless network such as one enabled using the Bluetooth® radio communication technology.

The first electronic device 1802 includes, among other computer components, one or more processing units (or processor(s)) 1808, a memory 1810, and a camera 1814. The processor 1808 may be implemented as appropriate in hardware, computer-executable instructions, software, firmware, or combinations thereof. Computer-executable instruction, software, or firmware implementations of the processor 1808 may include computer-executable or machine-executable instructions written in any suitable programming language to perform the various functions described.

The memory 1810 may include more than one memory. The memory 1810 may store program instructions that are loadable and executable on the processor(s) 1808, as well as data generated during the execution of these programs. Depending on the configuration and type of memory including the first electronic device 1802, the memory 1810 may be volatile (such as random access memory (RAM)) and/or non-volatile (such as read-only memory (ROM), flash memory, or other memory). The memory 1810 and any storage devices of the electronic device 1802 may include computer-readable storage media, such as Radom Access Memory (RAM), Read Only Memory (ROM), electrically erasable programmable read-only memory (EEPROM), hard drives, CD-ROMs, optical storage devices, magnetic storage devices, electronic non-volatile computer storage, for example Flash® memory, and other tangible storage media. Any of such computer-readable storage media can be configured to store instructions or program codes embodying aspects of the disclosure. The memory 1810 may also include computer-readable signal media. A computer-readable signal medium includes a propagated data signal with computer-readable program code embodied therein. Such a propagated signal takes any of a variety of forms including, but not limited to, electromagnetic, optical, or any combination thereof. A computer-readable signal medium includes any computer-readable medium that is not a computer-readable storage medium and that can communicate, propagate, or transport a program for use in connection with the electronic device 1802.

The memory 1810 may include an operating system and one or more application programs, modules, or services for implementing the techniques described herein including at least an application 1812A (e.g., a photo studio application).

The application 1812A may be configured to implement the techniques described herein with reference to FIGS. 22 and 23. In some examples, the first electronic device 1802 is configured to implement the techniques described with reference to these figures with or without an application similar to the application 1812A.

The camera 1814 may include any suitable combination of lenses, software, and the like capable of capturing images of objects within the portable photo studio. In some examples, the camera 1814 may be a back-facing camera or a front-facing camera.

The second electronic device 1804 includes, among other computer components, one or more processing units (or processor(s)) 1820 and a memory 1822, which may include an application 1812B. The processors 1820, the memory 1822, and the application 1812B are examples of the processors 1808, the memory 1810, and the application 1812A.

The computer system 1806 may include one or more service provider computers, perhaps arranged in a cluster of servers or as a server farm, and may host web service applications. These servers may be configured to host a website, application, or the similar viewable on the electronic device 1804. The computer system 1806 includes, among other computer components, one or more processing units (or processor(s)) 1824, a memory 1826, which may include an image processing application 1828, and image storage 1830. The processors 1824 and the memory 1826 are examples of the processors 1808 and the memory 1810.

The image processing application 1828 may be configured to process images received from the first electronic device 1802, as described in more detail with reference to FIG. 23. For example, the image processing application 1828 may receive raw image data and using computer vision techniques determine whether the image data represents one or more areas of interest. These areas of interest may be tagged and provided to a clinician for further evaluation. In some examples, the image processing application 1828 simply saves received image data (e.g., in the image storage 1830) for later evaluation by the clinician.

The image storage 1830 may be configured to store image data received from the first electronic device 1802. The image storage 1830 may include any suitable storage media and may store the data in any suitable format. For example, the image data may be stored in a database, with records associated with the users who captured the images (e.g., images may be associated with patients).

FIG. 19 illustrates an instruction user interface view 1900 of a photo studio application for use with a portable photo studio system, according to at least one example. The instruction user interface view 1900 may be presented at the electronic device 104 after the images of the user have been captured. In particular, the instruction user interface view 1900 may provide instructions for the user to review the images that were captured. In the instruction user interface view 1900 is presented an example of a suitable image 1902 and an example of a unsuitable image 1904. The instruction user interface view 1900 also includes reviewing user interface element 1906 and retake photo user interface element 1908. Both user interface elements (1906 and 1908) are presented as selectable buttons.

FIG. 20 illustrates a quality control user interface view 2000 of the photo studio application of FIG. 19, according to at least one example. The quality control user interface view 2000 is presented responsive to use selection of the reviewing user interface element 1906. The quality control user interface view 2000 includes an actual image 2002 captured during the image capture session. The quality control user interface view 2000 also includes a prompt 2004 relating to the actual image 2002 and options 2006 and 2008 for responding to the prompt 2004. If the image 2002 looks good (e.g., is suitable), the user may select the option 2008. If the image 2002 does not look good (e.g., is unsuitable), the user may select the option 2006. This process may be repeated for all images captured during the image capture session. In this manner, the user may decide which pictures need to be retaken and which are suitable.

FIG. 21 illustrates a flow chart showing the process 2100 for obtaining images of a human body using a portable photo studio system, according to at least one example. The process 2100 is performed by a purveyor of the portable photo studio system. This example will be discussed with respect to the example photo studio system shown in FIG. 1 but may be used with any suitable photo studio system according to this disclosure.

The process 2100 begins, at block 2102, by providing a photo studio system that includes a photo studio and an electronic device including a camera. In some examples, this may include providing the photo studio system to a participant in a photo clinical study.

At block 2104, the process 2100 includes providing instructions for assembling the photo studio system. In some examples, this may include at least one of providing printed instructions on parts of the photo studio, providing printed instructions separate from the photo studio, providing electronic instructions accessible on the electronic device, or providing electronic instructions accessible on a different electronic device.

At block 2106, the process 2100 includes providing instructions for orienting a portion of a human body within the photo studio. In some examples, this may include at least one of providing visual instructions via a screen of the electronic device or providing spoken instructions via a speaker of the electronic device.

At block 2108, the process 2100 includes enabling capture of images of the portion of the human body by the camera of the electronic device. In some examples, enabling capture of the images of the human body within the photo studio may include providing an application on the electronic device that operates the camera to capture the images.

At block 2110, the process 2100 includes enabling transmission of a portion of the images from the electronic device to a computer system. In some examples, enabling transmission of the portion of the images from the electronic device to the computer system may include providing an application on the electronic device that uploads the portion of the images to the computer system.

FIGS. 22 and 23 illustrate example flow diagrams showing processes 2200 and 2300, according to at least a few examples. These processes, and any other processes described herein, are illustrated as logical flow diagrams, each operation of which represents a sequence of operations that can be implemented in hardware, computer instructions, or a combination thereof. In the context of computer instructions, the operations may represent computer-executable instructions stored on one or more non-transitory computer-readable storage media that, when executed by one or more processors, perform the recited operations. Generally, computer-executable instructions include routines, programs, objects, components, data structures and the like that perform particular functions or implement particular data types. The order in which the operations are described is not intended to be construed as a limitation, and any number of the described operations can be combined in any order and/or in parallel to implement the processes.

Additionally, some, any, or all of the processes described herein may be performed under the control of one or more computer systems configured with specific executable instructions and may be implemented as code (e.g., executable instructions, one or more computer programs, or one or more applications) executing collectively on one or more processors, by hardware, or combinations thereof. As noted above, the code may be stored on a non-transitory computer readable storage medium, for example, in the form of a computer program including a plurality of instructions executable by one or more processors.

FIG. 22 illustrates a flow chart showing the process 2200 for obtaining images of a human body using a portable photo studio system, according to at least one example. The process 2200 may be performed by the application 1812 of the electronic device 1802. The process 2200 begins, at block 2202, by the electronic device 1802 providing first instructions for orientating a pair of human legs. The first instructions may be for orientating the pair of human legs into a first orientation with respect to a set of orientation indicia of a portable photo studio of the portable photo studio system. The first instructions may be spoken and provided via a speaker, visual and be provided via a screen and/or via one or more flashing lights.

At block 2204, the process 2200 includes the electronic device 1802 instructing capture of a first set of images of the pair of human legs in the first orientation. This may include instructing a camera of the electronic device 1802 to capture the first set of image. In some examples, the first set of images may include a single image, but may also include more than one image. For example, at the block 2204, the electronic device 1802 may capture just one image for the first orientation, which may later be evaluated before being uploaded. In some examples, at the block 2204, the electronic device 1802 may capture more than one image for the first orientation, and the user may later pick a "best image" out of the set including more than one image.

In some examples, the process 2200 further includes detecting that the pair of human legs is in the first orientation. In this example, the block 2204 may include capturing the first set of images responsive to detecting that the pair of human legs is in the first orientation. In some examples, the process 2200 further includes, after detecting that the pair of human legs is in the first orientation, generating, by the electronic device 1802, a notification representative of the pair of human legs being in the first orientation. For example, the electronic device 1802 may beep when the legs are in the correct orientation or may change a light from red to green.

At block 2206, the process 2200 includes the electronic device 1802 providing second instructions for orientating the pair of human legs. The second instructions may be for orientating the pair of human legs into a second orientation with respect to the set of orientation indicia. The second instructions may be provided in a manner similar to the first instructions at 2202, but for a different orientation.

In some examples, the set of orientation indicia may be visible on a bottom section of the portable photo studio and may include heel indicia, orientation indicia of a first type, and orientation indicia of a second type. In this example, the heel indicia, the orientation indicia of the first type, and the orientation indicia of the second type may be divided into two reference indicium groups. The first orientation and the second orientation may be selecting from a group of orientations including a first orientation in which a pair of feet of the pair of human legs is oriented with heels on the heel indicia and toes pointing toward the electronic device. The group may also include a second orientation in which the pair of feet oriented with heels on the heel indicia, toes of a first foot of the pair of feet pointing toward the electronic device, and toes of a second foot of the pair of feet pointing substantially perpendicular with respect to the toes of the first foot. The group may also include a third orientation in which the pair of feet is oriented with heels on the heel indicia, the toes of the second foot pointing toward the electronic device, and the toes of the second foot pointing substantially perpendicular with respect to the toes of the second foot. The group may also include a fourth orientation in which the pair of feet is oriented with heels on the heel indicia, the toes of the second foot pointing opposite the electronic device, and the toes of the first foot pointing substantially perpendicular with respect to the toes of the second foot. The group may also include a fifth orientation in which the pair of feet is oriented with heels on the heel indicia, the toes of the first foot pointing opposite the electronic device, and the toes of the second foot pointing substantially perpendicular with respect to the toes of the first foot.

At block 2208, the process 2200 includes the electronic device 1802 instructing capture of a second set of images of the pair of human legs in the second orientation. This may include instructing the camera of the electronic device 1802 to capture the second set of images. The second set of images may have similar characteristics as the first set of images captured at the block 2204, but for a different (e.g., the second) orientation.

At block 2210, the process 2200 includes the electronic device 1802 providing the first set of images and/or the second set of images for review. For example, the first set of images and the second set of images may be provided for display at a screen of the electronic device. Reviewing the images of the first set and second set may including requesting user selection of individual images of the first and second set of images to define a portion of the first and second sets of images, and determining the portion of the first and second sets of images based at least in part on the user selection of the individual images. In some examples, the process 2200 further includes, prior to providing the first and second sets of images for presentation at the screen of the electronic device, providing, for presentation at the screen of the electronic device, instructions for selecting images (e.g., using the user interface view 1900).

If at the review block 2210, the user determines that one or more images are unsuitable and depending on which images mapping to which orientations are unsuitable, the process 2200 may return to an earlier block to obtain additional images. For example, as illustrated in FIG. 22, the process 2200 may return to the block 2204 to capture images of the pair of legs in the first orientation (e.g., assuming the images of the legs in the first orientation are unsuitable).

At block 2212, the process 2200 includes uploading at least a portion of the first and second sets of images. In some examples, this may include the electronic device 1802 uploading to an external system (e.g., the computer system 1806). The portion of the images may include those that the user has selected as suitable at the block 2210 (e.g., using the quality control user interface view 2000). In some examples, uploading at least the portion of the first and second sets of images may include uploading raw data corresponding to the portion of the first and second sets of images.

FIG. 23 illustrates a flow chart showing the process 2300 for conducting an image capture session using a portable photo studio system and evaluating images of an area of interest, according to at least one example. The process 2300 may be implemented by the image processing application 1828 of the computer system 1806.

The process 2300 begins, at block 2302, by the computer system 1806 requesting an image capture session using a portable photo studio system. The portable photo studio system may include a portable photo studio apparatus forming a unicolor background, an electronic device removably mountable to the portable photo studio apparatus, and a color card mountable to the photo studio apparatus in an orientation that opposes the electronic device. The color card may include a plurality of reference colors. In some examples, requesting the image capture session may be performed by sending the request to a first electronic device such as a personal electronic device, which is different from the electronic device included in the portable photo studio system. For example, the electronic device may be a fungible electronic device.

At block 2304, the process 2300 includes the computer system 1806 receiving image data corresponding to a plurality of images obtained during the image capture session. The image data may be received from the electronic device. The image data, for each image of the plurality of images, may represent at least (i) a human body part in an orientation, (ii) the color card including the plurality of reference colors, and (iii) the unicolor background in front of which the human body part is positioned. In some examples, the image data is raw image data.

At block 2306, the process 2300 includes using at least one of the reference colors of the plurality of reference colors to identify an area of interest on the body part. The area of interest may be a visible symptom of a potential skin condition, a color of the body part, or any other feature visible in the image data. This may include using computer vision algorithm(s) to recognize objects, identify objects, and/or detect objects and/or other features present in the images. For example, any suitable image processing technique may be implemented to identify the area of interest (e.g., edge detection, blob detection, etc.).

At block 2308, the process 2300 includes tagging the area of interest. Tagging the area of interest may include notating the image data at the location relating to the area of interest. For example, an image annotation algorithm, which may also perform the block 2306, may assign metadata and/or graphics to aspects of the digital image. For example, areas of interest may be highlighted with a graphical overlay or graphical element. In some examples, the tagging the area of interest identifies some characteristic of the image identified at the block 2308. For example, tagging the area of interest may include identifying the image as being of a set of legs or other object.

FIG. 24 illustrates examples of components of a computer system 2400, according to at least one example. The computer system 2400 may be a single computer such as a user computing device and/or can represent a distributed computing system such as one or more server computing devices. The computer system 2400 is an example of the computing devices 104, 116, 1802, 1804, and 1806.

The computer system 2400 may include at least a processor 2402, a memory 2404, a storage device 2406, input/output peripherals (I/O) 2408, communication peripherals 2410, and an interface bus 2412. The interface bus 2412 is configured to communicate, transmit, and transfer data, controls, and commands among the various components of the computer system 2400. The memory 2404 and the storage device 2406 include computer-readable storage media, such as Radom Access Memory (RAM), Read ROM, electrically erasable programmable read-only memory (EE-PROM), hard drives, CD-ROMs, optical storage devices, magnetic storage devices, electronic non-volatile computer storage, for example Flash® memory, and other tangible storage media. Any of such computer-readable storage media can be configured to store instructions or program codes embodying aspects of the disclosure. The memory 2404 and the storage device 2406 also include computer-readable signal media. A computer-readable signal medium includes a propagated data signal with computer-readable program code embodied therein. Such a propagated signal takes any of a variety of forms including, but not limited to, electromagnetic, optical, or any combination thereof. A computer-readable signal medium includes any computer-readable medium that is not a computer-readable storage medium and that can communicate, propagate, or transport a program for use in connection with the computer system 2400.

Further, the memory 2404 includes an operating system, programs, and applications. The processor 2402 is configured to execute the stored instructions and includes, for example, a logical processing unit, a microprocessor, a digital signal processor, and other processors. The memory 2404 and/or the processor 2402 can be virtualized and can be hosted within another computing system of, for example, a cloud network or a data center. The I/O peripherals 2408 include user interfaces, such as a keyboard, screen (e.g., a touch screen), microphone, speaker, other input/output devices, and computing components, such as graphical processing units, serial ports, parallel ports, universal serial buses, and other input/output peripherals. The I/O peripherals 2408 are connected to the processor 2402 through any of the ports coupled to the interface bus 2412. The communication peripherals 2410 are configured to facilitate communication between the computer system 2400 and other computing devices over a communications network and include, for example, a network interface controller, modem, wireless and wired interface cards, antenna, and other communication peripherals.

In the following, further examples are described to facilitate the understanding of the present disclosure.

Example 1. In this example, there is provided an apparatus, including:
- a bottom including a first edge;
- a first side wall pivotably connected to the bottom at a first hinge;
- a second side wall pivotably connected to the first side wall at a second hinge;
- a third side wall pivotably connected to the first side wall at a third hinge, the third hinge opposite the second hinge, wherein the first side wall, the second side wall, and the third side wall are respectively pivotable about the first hinge, the second hinge, and the third hinge between an unassembled state and an assembled state in which the first side wall, the second side wall, and the third side wall form a U shape; and
- an electronics stand pivotably connected to the first edge at a fourth hinge, the electronics stand including a pocket sized and configured to receive and support an electronic device, wherein the electronics stand is pivotable about the fourth hinge between the unassembled state and the assembled state in which the electronics stand faces the U shape.

Example 2. In this example, there is provided an apparatus of any of the preceding or subsequent examples, wherein the bottom, the first side wall, the second side wall, the third side wall, and the electronics stand are formed from a single piece of planar material.

Example 3. In this example, there is provided an apparatus of any of the preceding or subsequent examples, wherein each of the first hinge, the second hinge, the third hinge, and the fourth hinge is formed as a crease in the single piece of planar material.

Example 4. In this example, there is provided an apparatus of any of the preceding or subsequent examples, wherein at least one of the first hinge, the second hinge, the third hinge, or the fourth hinge includes a creased hinge, a zippered hinge, a taped hinge, a slit hinge, or a perforated hinge.

Example 5. In this example, there is provided an apparatus of any of the preceding or subsequent examples, further including a color card connected to at least one of the first side wall, the second side wall, or the third side wall.

Example 6. In this example, there is provided an apparatus of any of the preceding or subsequent examples, wherein the color card includes a plurality of reference color blocks positioned on a first side of the color card, and wherein the first side of the color card faces the electronics stand in the assembled state.

Example 7. In this example, there is provided an apparatus of any of the preceding or subsequent examples, wherein the color card is moveable from a collapsed state to a presented state responsive to at least one of the first side wall or the second side wall being pivoted respectively about the second hinge or the third hinge.

Example 8. In this example, there is provided an apparatus of any of the preceding or subsequent examples, wherein the color card is connected to the at least one of the first side wall, the second side wall, or the third side wall at a height that is substantially midway between a bottom edge and a top edge of the at least one of the first side wall, the second side wall, and the third side wall.

Example 9. In this example, there is provided an apparatus of any of the preceding or subsequent examples, wherein a perpendicular distance between the first hinge and the color card is between 300 mm and 400 mm.

Example 10. In this example, there is provided an apparatus of any of the preceding or subsequent examples, wherein one or more openings are formed in the bottom that, when in the unassembled state, form a handle for carrying the apparatus.

Example 11. In this example, there is provided an apparatus of any of the preceding or subsequent examples, wherein the bottom includes a plurality of reference indicia that, when in the assembled state, is positioned between the second side wall and the third side wall.

Example 12. In this example, there is provided an apparatus of any of the preceding or subsequent examples, wherein the plurality of reference indicia comprise heel indicia, orientation indicia of a first type, and orientation indicia of a second type, and wherein the heel indicia, the orientation indicia of the first type, and the orientation indicia of the second type are divided into two reference indicium groups.

Example 13. In this example, there is provided an apparatus of any of the preceding or subsequent examples, wherein a first reference indicium group of the two reference indicium groups includes a first heel indicator, one orientation indicium of the first type, and two orientation indicia of the second type, and wherein a second reference indicium group of the two reference indicium groups includes a second heel indicator, one orientation indicium of the second type, and two orientation indicia of the first type.

Example 14. In this example, there is provided an apparatus of any of the preceding or subsequent examples, wherein the heel indicia are positioned on the bottom along a centerline extending between a midpoint of the second side wall and a midpoint of the third side wall.

Example 15. In this example, there is provided an apparatus of any of the preceding or subsequent examples, wherein a perpendicular distance between the centerline and the fourth hinge is between 750 mm and 850 mm.

Example 16. In this example, there is provided an apparatus of any of the preceding or subsequent examples, wherein the electronics stand includes:
  a main body section in which is formed the pocket;
  a first wing section pivotably connected to the main body section via a fifth hinge; and
  a second wing section pivotably connected to the main body section via a sixth hinge, wherein each of the first wing section and the second wing section is respectively pivotable about the fifth hinge and the sixth hinge to hold the electronics stand in an upright position when in the assembled state.

Example 17. In this example, there is provided an apparatus of any of the preceding or subsequent examples, wherein in the unassembled state:
  each of the second side wall and the third side wall is pivotable respectively about the second hinge and third hinge until the second side wall and the third side wall overlay the first side wall;
  the first side wall is pivotable about the first hinge until each of the first side wall, the second side wall, and the third side wall overlay a first section of the bottom; and
  a second section of the bottom is pivotable about a sixth hinge pivotably connecting the first section of the bottom and the second section of the bottom until the second section of the bottom overlays the first section of the bottom.

Example 18. In this example, there is provided an apparatus of any of the preceding or subsequent examples, wherein, in the assembled state:
  the bottom is supportable by a support surface;
  the first side wall is pivotable about the first hinge to form a back wall of the U shape;
  the second side wall is pivotable about the second hinge to form a first leg of the U shape; and
  the third side wall is pivotable about the third hinge to form a second leg of the U shape.

Example 19. In this example, there is provided an apparatus of any of the preceding or subsequent examples, wherein the second side wall and the third side wall have substantially the same surface area.

Example 20. In this example, there is provided a method, including:
  rotating, at a first hinge, a first part of a bottom of the portable photo studio into an open position, the portable photo studio including:
    the bottom;
    a background section including a first wall, a second wall, and a third wall; and
    an electronics stand;
  rotating, at a second hinge, the background section into an open position, wherein the second hinge is integrally formed between a second part of the bottom and the first wall;
  rotating, at a third hinge, the second wall into an open position, wherein the third hinge is integrally formed between the first wall and the second wall;
  rotating, at a fourth hinge, the third wall into an open position, wherein the fourth hinge is integrally formed between the first wall and the third wall; and
  rotating, at a fifth hinge, the electronics stand into an open position, wherein the fifth hinge is integrally formed between the first part of the bottom and the electronics stand.

Example 21. In this example, there is provided a method of any of the preceding or subsequent examples, wherein the bottom, the background section, and the electronics stand are formed from a single piece of planar material, and wherein each of the first hinge, the second hinge, the third hinge, the fourth hinge, and fifth hinge is formed as a crease in the single piece of planar material.

Example 22. In this example, there is provided a method of any of the preceding or subsequent examples, wherein the portable photo studio includes a color card connected to at least one of the first wall or the second wall, and wherein rotating the second wall reveals the color card.

Example 23. In this example, there is provided a method of any of the preceding or subsequent examples, wherein the first hinge is integrally formed between the first part of the bottom and the second part of the bottom.

Example 24. In this example, there is provided a method of any of the preceding or subsequent examples, further including:
  rotating, at a sixth hinge, a first wing section of the electronics stand into an open position, wherein the sixth hinge is integrally formed between the first wing section and a main body section of the electronics stand; and
  rotating, at a seventh hinge, a second wing section of the electronics stand into an open position, wherein the seventh hinge is integrally formed between the second wing section and the main body section.

Example 25. In this example, there is provided a method of any of the preceding or subsequent examples, further including, after rotating the electronics stand into the open position, mounting an electronic device in the electronics stand, wherein the electronics stand supports the electronic device in a substantially perpendicular orientation with respect to the bottom.

Example 26. In this example, there is provided a method of any of the preceding or subsequent examples, wherein, in the open positions, the first wall, the second wall, and the third wall form a U shape, with the electronics stand opposing the U shape.

Example 27. In this example, there is provided a method of any of the preceding or subsequent example, further including mounting an auxiliary light to the bottom at a position that is adjacent to the electronics stand.

Example 28. In this example, there is provided a method of setting up a portable photo studio, including:
- rotating, at a first hinge integrally formed in the portable photo studio, a first part of a bottom section of the portable photo studio;
- rotating, at a plurality of hinges integrally formed in the portable photo studio, a background section of the portable photo studio to define a U-shaped cavity, wherein at least two edges of the background section physically contact the bottom section when the background section defines the U-shaped cavity; and
- rotating, at a second hinge, an electronics stand into an orientation that opposes the U-shaped cavity, wherein the second hinge is integrally formed between the first part of the bottom section and the electronics stand.

Example 29. In this example, there is provided a method of any of the preceding or subsequent examples, wherein the background section includes three side walls formed from a single piece of planar material.

Example 30. In this example, there is provided a method of any of the preceding or subsequent examples, wherein a first edge of a first side wall and a second edge of a second side wall of the three side walls contacts the bottom section when the background section defines the U-shaped cavity.

Example 31. In this example, there is provided a method of any of the preceding or subsequent examples, wherein a first side wall of the three side walls is connected to the bottom section via a third hinge, a second side wall of the three side walls is connected to the first side wall via a fourth hinge, and a third side wall of the three side walls is connected to the first side wall via a fifth hinge.

Example 32. In this example, there is provided a method of any of the preceding or subsequent examples, further including placing the portable photo studio against a wall with the U-shaped cavity opening away from the wall.

Example 33. In this example, there is provided a method of any of the preceding or subsequent examples, wherein the portable photo studio includes instructions printed thereon for rotating the first part, rotating the background section, and rotating the electronics stand.

Example 34. In this example, there is provided a method of forming a portable photo studio, including:
- providing a piece of planar material;
- forming, in the piece of planar material, a background section including a plurality of panels, a bottom section connected to the background section, and an electronics stand connected to the bottom section;
- forming, in the piece of planar material, a first hinge between the bottom section and a first panel of the plurality of panels;
- forming, in the piece of planar material, a second hinge between the first panel and a second panel of the plurality of panels;
- forming, in the piece of planar material, a third hinge between the first panel and a third panel of the plurality of panels;
- forming, in the electronics stand of the piece of planar material, a pair of support stands and a pocket configured to receive and support an electronic device; and
- forming, in the piece of planar material, a fourth hinge between the bottom section and the electronics stand.

Example 35. In this example, there is provided a method of any of the preceding or subsequent examples, further including connecting a color card to at least one of the first panel or the second panel.

Example 36. In this example, there is provided a method of any of the preceding or subsequent examples, further including forming one or more elongate openings in the bottom section at a position between the fifth hinge and the first hinge.

Example 37. In this example, there is provided a method of any of the preceding or subsequent examples, further including applying a plurality of reference indicia to the bottom section.

Example 38. In this example, there is provided a method of any of the preceding or subsequent examples, further including painting at least one side of each of the bottom section, the first panel, the second panel, and the third panel the same color.

Example 39. In this example, there is provided a method of any of the preceding or subsequent examples, wherein the same color is a Pantone® Cool Gray color.

Example 40. In this example, there is provided a method of any of the preceding or subsequent examples, further including, after providing the piece of planar material, cutting the piece of planar material to define the bottom section, the first panel, the second panel, the third panel, and the electronics stand.

Example 41. In this example, there is provided a method of any of the preceding or subsequent examples, wherein forming the electronics stand includes forming the pocket by at least:
- cutting a pocket-forming section from the electronics stand, the pocket-forming section including a body and a pair of tabs connected to the body;
- folding the pocket-forming section at a fifth hinge formed between the body and the electronics stand; and
- connecting the pair of tabs to the electronics stand.

Example 42. In this example, there is provided a method of any of the preceding or subsequent examples, further including:
- folding each of the first panel, the second panel, and the third panel at least until each of the first panel, the second panel, and the third panel overlap a first part of the bottom section;
- folding the electronics stand at least until the electronics stand overlaps a second part of the bottom section; and
- folding the second part of the bottom section at least until the second part overlaps the first panel.

Example 43. In this example, there is provided an apparatus, including:
- light-reflecting means for reflecting light during image capturing;
- supporting means for supporting an electronic device and orienting a camera of the electronic device towards the light-reflecting means;
- supporting means for supporting a light source oriented towards the reflecting means; and
- orienting means for directing orientations of a user with respect to the supporting means.

Example 44. In this example, there is provided a system, including:
- a portable photo studio, including:
  - a bottom section;
  - a background section pivotably connected to the bottom section and including a plurality of walls that are pivotable with respect to each other to define a U shape; and an electronics stand pivotably connected to the bottom section and pivotable with respect to the bottom section into an upright orientation that opposes the U shape, the electronics stand including a mounting pocket; and an electronic device removably mountable within the mounting pocket of the electronics stand, wherein the electronic device, when mounted in the mounting pocket, orients a camera of the electronic device toward the U shape.

Example 45. In this example, there is provided a system of any of the preceding or subsequent examples, wherein the electronic device includes a processor and a memory including computer-executable instructions that, when executed by the processor cause the electronic device to, at least:

instruct a user to orient a portion of a human body within the portable photo studio;

cause the camera to capture images of the portion of the human body; and transmit a portion of the images to an external computer system.

Example 46. In this example, there is provided a system of any of the preceding or subsequent examples, wherein the bottom section includes a plurality of reference indicia, and wherein instructing the user to orient the portion of the human body includes instructing the user to orient the portion of the human body with respect to the plurality of reference indicia.

Example 47. In this example, there is provided a system of any of the preceding or subsequent examples, wherein instructing the user to orient the portion of the human body includes providing visual instructions via a screen of the electronic device.

Example 48. In this example, there is provided a system of any of the preceding or subsequent examples, wherein instructing the user to orient the portion of the human body includes providing verbal instructions via a speaker of the electronic device.

Example 49. In this example, there is provided a system of any of the preceding or subsequent examples, wherein the portion of the human body includes one or more legs.

Example 50. In this example, there is provided a system of any of the preceding or subsequent examples, wherein the electronic device, when mounted in the mounting pocket, positions a field of view of the camera on the one or more legs.

Example 51. In this example, there is provided a system of any of the preceding or subsequent examples, wherein the electronic device is a mobile phone.

Example 52. In this example, there is provided a system of any of the preceding or subsequent examples, further including an auxiliary light removably mountable in the bottom section or the electronics stand, and wherein the auxiliary light, when mounted, orients a light source of the auxiliary light towards the U shape.

Example 53. In this example, there is provided a system of any of the preceding or subsequent examples, further including a color card pivotably connected to the background section.

Example 54. In this example, there is provided a system of any of the preceding or subsequent examples, wherein the color card includes a plurality of reference color blocks positioned on a first side that opposes the electronics stand when the color card is pivoted into an open position.

Example 55. In this example, there is provided a system of any of the preceding or subsequent examples, wherein the portable photo studio is configured to receive a human user onto the bottom section and into a volume defined by the background section in the U shape and the bottom section.

Example 56. In this example, there is provided a system of any of the preceding or subsequent examples, wherein the plurality of walls comprise:

a first side wall pivotably connected to the bottom section at a first hinge;

a second side wall pivotably connected to the first side wall at a second hinge;

a third side wall pivotably connected to the first side wall at a third hinge, the third hinge opposite the second hinge.

Example 57. In this example, there is provided a system of any of the preceding or subsequent examples, wherein the electronics stand comprise a pair of wing sections pivotable with respect to the mounting pocket to hold the electronics stand in the upright orientation.

Example 58. In this example, there is provided a method, including:

providing a photo studio system that includes:
 a photo studio; and
 an electronic device including a camera;

providing instructions for assembling the photo studio system;

providing instructions for orienting a portion of a human body within the photo studio;

enabling capture of images of the portion of the human body by the camera of the electronic device; and enabling transmission of a portion of the images from the electronic device to a computer system.

Example 59. In this example, there is provided a method of any of the preceding or subsequent examples, wherein providing the photo studio includes providing the photo studio system to a participant in a photo clinical study.

Example 60. In this example, there is provided a method of any of the preceding or subsequent examples, wherein providing the instructions for assembling the photo studio system includes at least one of providing printed instructions on parts of the photo studio, printed instructions separate from the photo studio, electronic instructions accessible on the electronic device, or electronic instructions accessible on a different electronic device.

Example 61. In this example, there is provided a method of any of the preceding or subsequent examples, wherein providing the instructions for orienting the portion of the human body within the photo studio includes at least one of providing visual instructions via a screen of the electronic device or providing spoken instructions via a speaker of the electronic device.

Example 62. In this example, there is provided a method of any of the preceding or subsequent examples, wherein enabling the capture of the images of the human body within the photo studio includes providing an application on the electronic device that operates the camera to capture the images.

Example 63. In this example, there is provided a method of any of the preceding or subsequent examples, wherein enabling the transmission of the portion of the images from the electronic device to the computer system includes providing an application on the electronic device that uploads the portion of the images to the computer system.

Example 64. In this example, there is provided a computer-implemented method, including:

providing, by an electronic device of a portable photo studio system, first instructions for orientating a pair of human legs into a first orientation with respect to a set of orientation indicia of a portable photo studio of the portable photo studio system;

capturing, by a camera of the electronic device, a first set of images of the pair of human legs in the first orientation;

providing, by the electronic device, second instructions for orientating the pair of human legs into a second orientation with respect to the set of orientation indicia;

capturing, by the camera of the electronic device, a second set of images of the pair of human legs in the second orientation; and uploading, by the electronic device and to an external system, at least a portion of the first set of images and the second set of images.

Example 65. In this example, there is provided a computer-implemented method of any of the preceding or subsequent examples, wherein providing the first instructions and the second instructions includes providing the first instructions and the second instructions via a speaker or a screen of the electronic device.

Example 66. In this example, there is provided a computer-implemented method of any of the preceding or subsequent examples, further including detecting that the pair of human legs is in the first orientation, and wherein capturing the first set of images includes capturing the first set of images responsive to detecting that the pair of human legs is in the first orientation.

Example 67. In this example, there is provided a computer-implemented method of any of the preceding or subsequent examples, further including, after detecting that the pair of human legs is in the first orientation, generating, by the electronic device, a notification representative of the pair of human legs being in the first orientation.

Example 68. In this example, there is provided a computer-implemented method of any of the preceding or subsequent examples, wherein uploading at least the portion of the first set of images and the second set of images includes uploading raw data corresponding to the portion of the first set of images and the second set of images.

Example 69. In this example, there is provided one or more non-transitory computer-readable storage devices including computer-executable instructions that, when executed by one or more processors, cause the one or more processors to perform operations including:

providing, by an electronic device of a portable photo studio system, first instructions for orientating a human body part into a first orientation with respect to a set of orientation indicia of a portable photo studio of the portable photo studio system;

instructing capture, by a camera of the electronic device, a first set of images of the human body part in the first orientation;

providing, by the electronic device, second instructions for orientating the human body part into a second orientation with respect to the set of orientation indicia;

instructing capture, by the camera of the electronic device, a second set of images of the human body part in the second orientation; and uploading, by the electronic device and to an external system, at least a portion of the first set of images and the second set of images.

Example 70. In this example, there is provided one or more non-transitory computer-readable storage devices of any of the preceding or subsequent examples, wherein the instructions further cause the one or more processors to perform additional operations including determining the portion of the first and second sets of images by at least:

providing the first set of images and the second set of images for presentation at a screen of the electronic device;

requesting user selection of individual images of the first set of images and the second set of images to define the portion of the first set of images and the second set of images; and determining the portion of the first set of images and the second set of images based at least in part on the user selection of the individual images.

Example 71. In this example, there is provided one or more non-transitory computer-readable storage devices of any of the preceding or subsequent examples, wherein the instructions further cause the one or more processors to perform additional operations including, prior to providing the first set of images and the second set of images for presentation at the screen of the electronic device, providing, for presentation at the screen of the electronic device, instructions for selecting images.

Example 72. In this example, there is provided one or more non-transitory computer-readable storage devices of any of the preceding or subsequent examples, wherein the set of orientation indicia are visible on a bottom section of the portable photo studio and comprise heel indicia, orientation indicia of a first type, and orientation indicia of a second type, and wherein the heel indicia, the orientation indicia of the first type, and the orientation indicia of the second type are divided into two reference indicium groups.

Example 73. In this example, there is provided one or more non-transitory computer-readable storage devices of any of the preceding or subsequent examples, wherein the human body part includes a pair of human legs, and wherein the first orientation and the second orientation are selecting from a group of orientations including:

a pair of feet of the pair of human legs is oriented with heels on the heel indicia and toes pointing toward the electronic device;

the pair of feet oriented with heels on the heel indicia, toes of a first foot of the pair of feet pointing toward the electronic device, and toes of a second foot of the pair of feet pointing substantially perpendicular with respect to the toes of the first foot;

the pair of feet oriented with heels on the heel indicia, the toes of the second foot pointing toward the electronic device, and the toes of the second foot pointing substantially perpendicular with respect to the toes of the second foot;

the pair of feet oriented with heels on the heel indicia, the toes of the second foot pointing opposite the electronic device, and the toes of the first foot pointing substantially perpendicular with respect to the toes of the second foot; and the pair of feet oriented with heels on the heel indicia, the toes of the first foot pointing opposite the electronic device, and the toes of the second foot pointing substantially perpendicular with respect to the toes of the first foot.

Example 74. In this example, there is provided a computer-implemented method, including:

requesting an image capture session using a portable photo studio system that includes:
  a portable photo studio apparatus forming a unicolor background;
  an electronic device removably mountable to the portable photo studio apparatus; and a color card mountable to the portable photo studio apparatus in an orientation that opposes the electronic device, the color card including a plurality of reference colors;

receiving, from the electronic device, image data corresponding to a plurality of images obtained during the image capture session, the image data, for each image of the plurality of images, representing at least (i) a human body part in an orientation, (ii) the color card comprising the plurality of reference colors, and (iii) the unicolor background in front of which the human body part is positioned; and using at least one of the reference colors of the plurality of reference colors to identify an area of interest on the body part.

Example 75. In this example, there is provided a method of any of the preceding or subsequent examples, wherein the electronic device is a first electronic device, and wherein requesting the image capture session includes sending a request to a second electronic device.

Example 76. In this example, there is provided a method of any of the preceding or subsequent examples, wherein the first electronic device is a fungible electronic device and the second electronic device is a personal electronic device.

Example 77. In this example, there is provided a method of any of the preceding or subsequent examples, wherein receiving the image data includes receiving the image data in a raw format.

Example 78. In this example, there is provided a method of any of the preceding or subsequent examples, wherein the area of interest includes a visible symptom of a potential skin condition.

The specification and drawings are, accordingly, to be regarded in an illustrative rather than a restrictive sense. It will, however, be evident that various modifications and changes may be made thereunto without departing from the broader spirit and scope of the disclosure as set forth in the claims.

Other variations are within the spirit of the present disclosure. Thus, while the disclosed techniques are susceptible to various modifications and alternative constructions, certain illustrated examples thereof are shown in the drawings and have been described above in detail. It should be understood, however, that there is no intention to limit the disclosure to the specific form or forms disclosed, but on the contrary, the intention is to cover all modifications, alternative constructions and equivalents falling within the spirit and scope of the disclosure, as defined in the appended claims.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, it should be understood that the present disclosure has been presented for purposes of example rather than limitation, and does not preclude inclusion of such modifications, variations, and/or additions to the present subject matter as would be readily apparent to one of ordinary skill in the art. Indeed, the methods and systems described herein may be embodied in a variety of other forms; furthermore, various omissions, substitutions and changes in the form of the methods and systems described herein may be made without departing from the spirit of the present disclosure. The accompanying claims and their equivalents are intended to cover such forms or modifications as would fall within the scope and spirit of the present disclosure.

Unless specifically stated otherwise, it is appreciated that throughout this specification discussions utilizing terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed herein are not limited to any particular hardware architecture or configuration. A computing device can include any suitable arrangement of components that provide a result conditioned on one or more inputs. Suitable computing devices include multipurpose microprocessor-based computing systems accessing stored software that programs or configures the computing system from a general purpose computing apparatus to a specialized computing apparatus implementing one or more embodiments of the present subject matter. Any suitable programming, scripting, or other type of language or combinations of languages may be used to implement the teachings contained herein in software to be used in programming or configuring a computing device.

Embodiments of the methods disclosed herein may be performed in the operation of such computing devices. The order of the blocks presented in the examples above can be varied—for example, blocks can be re-ordered, combined, and/or broken into sub-blocks. Certain blocks or processes can be performed in parallel.

The use of the terms "a" and "an" and "the" and similar referents in the context of describing the disclosed examples (especially in the context of the following claims) are to be construed to cover both the singular and the plural, unless otherwise indicated herein or clearly contradicted by context. The terms "comprising," "having," "including," and "containing" are to be construed as open-ended terms (e.g., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate examples of the disclosure and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is otherwise understood within the context as used in general to present that an item, term, etc., may be either X, Y, or Z, or any combination thereof (e.g., X, Y, and/or Z). Thus, such disjunctive language is not generally intended to, and should not, imply that certain examples require at least one of X, at least one of Y, or at least one of Z to each be present.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and all three of A and B and C.

Preferred examples of this disclosure are described herein, including the best mode known to the inventors for carrying out the disclosure. Variations of those preferred examples may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A computer-implemented method, comprising:
   providing, by an electronic device of a portable photo studio system, first instructions for orientating a human body part into a first orientation with respect to a set of orientation indicia of a portable photo studio of the portable photo studio system;
   capturing, by a camera of the electronic device, a first set of images of the human body part in the first orientation;
   providing, by the electronic device, second instructions for orientating the human body part into a second orientation with respect to the set of orientation indicia;
   capturing, by the camera of the electronic device, a second set of images of the human body part in the second orientation; and
   uploading, by the electronic device and to an external system, at least a portion of the first set of images and the second set of images.

2. The computer-implemented method of claim 1, wherein:
   providing the first instructions and the second instructions comprises providing the first instructions and the second instructions via a speaker or a screen of the electronic device; and
   the first instructions and the second instructions are provided with respect to markings on a bottom section of the portable photo studio.

3. One or more non-transitory computer-readable storage devices comprising computer-executable instructions that, when executed by one or more processors, cause the one or more processors to perform operations comprising:
   providing, by an electronic device of a portable photo studio system, first instructions for orientating a human body part into a first orientation with respect to a set of orientation indicia of a portable photo studio of the portable photo studio system;
   instructing capture, by a camera of the electronic device, a first set of images of the human body part in the first orientation;
   providing, by the electronic device, second instructions for orientating the human body part into a second orientation with respect to the set of orientation indicia;
   instructing capture, by the camera of the electronic device, a second set of images of the human body part in the second orientation; and
   uploading, by the electronic device and to an external system, at least a portion of the first set of images and the second set of images.

4. The one or more non-transitory computer readable storage devices of claim 3, wherein the set of orientation indicia are visible on a bottom section of the portable photo studio and comprise heel indicia, orientation indicia of a first type, and orientation indicia of a second type, and wherein the heel indicia, the orientation indicia of the first type, and the orientation indicia of the second type are divided into two reference indicium groups.

5. The one or more non-transitory computer readable storage devices of claim 4, wherein:
   the human body part comprises a pair of human legs;
   the first orientation and the second orientation are selected from a group of orientations comprising:
      a pair of feet of the pair of human legs is oriented with heels on the heel indicia and toes pointing toward the electronic device;
      the pair of feet oriented with heels on the heel indicia, toes of a first foot of the pair of feet pointing toward the electronic device, and toes of a second foot of the pair of feet pointing substantially perpendicular with respect to the toes of the first foot;
      the pair of feet oriented with heels on the heel indicia, the toes of the second foot pointing toward the electronic device, and the toes of the second foot pointing substantially perpendicular with respect to the toes of the second foot;
      the pair of feet oriented with heels on the heel indicia, the toes of the second foot pointing opposite the electronic device, and the toes of the first foot pointing substantially perpendicular with respect to the toes of the second foot; and
      the pair of feet oriented with heels on the heel indicia, the toes of the first foot pointing opposite the electronic device, and the toes of the second foot pointing substantially perpendicular with respect to the toes of the first foot; and
   comprising computer-executable instructions that, when executed by the one or more processors, cause the one or more processors to perform operations further comprising detecting that the pair of human legs is in the first orientation, wherein capturing the first set of images comprises capturing the first set of images responsive to detecting that the pair of human legs is in the first orientation.

6. A system comprising:
   one or more processors; and
   one or more computer-readable storage media storing computer-executable instructions which, when executed by the one or more processors, cause the one or more processors to perform operations including:
      providing, by an electronic device of a portable photo studio system, first instructions for orientating a human body part into a first orientation with respect to a set of orientation indicia of a portable photo studio of the portable photo studio system;
      instructing capture, by a camera of the electronic device, a first set of images of the human body part in the first orientation;

providing, by the electronic device, second instructions for orientating the human body part into a second orientation with respect to the set of orientation indicia;

instructing capture, by the camera of the electronic device, a second set of images of the human body part in the second orientation; and uploading, by the electronic device and to an external system, at least a portion of the first set of images and the second set of images.

7. The system of claim 6, wherein the first set of images includes a plurality of images, and the computer-executable instructions further cause the one or more processors to perform additional operations comprising:

providing the plurality of images for presentation at a screen of the electronic device;

requesting user selection of a best image of the plurality of images to define the portion of the first set of images; and determining the portion of the first set of images based at least in part on the user selection of the best image of the plurality of images.

8. The system of claim 6, wherein the computer-executable instructions further cause the one or more processors to perform additional operations comprising:

providing the first set of images and the second set of images for presentation at a screen of the electronic device;

requesting user selection of individual images of the first set of images and the second set of images to define the portion of the first set of images and the second set of images; and determining the portion of the first set of images and the second set of images based at least in part on the user selection of the individual images; and responsive to an empty user selection:
  instructing capture, by the camera of the electronic device, of additional images for the first set of images of the human body part in the first orientation; and
  instructing capture, by the camera of the electronic device, of additional images for the second set of images of the human body part in the second orientation.

9. The system of claim 6, wherein:
the computer-executable instruction for capturing the first set of images is responsive to a first voice command instructing the camera to capture the first set of images;
the computer-executable instruction for capturing the second set of images is responsive to a second voice command instructing the camera to capture the second set of images; and
the electronic device includes a voice assistant.

10. The method of claim 1, wherein the set of orientation indicia are visible on a bottom section of the portable photo studio and comprise heel indicia, orientation indicia of a first type, and orientation indicia of a second type, and wherein the heel indicia, the orientation indicia of the first type, and the orientation indicia of the second type are divided into two reference indicium groups.

11. The method of claim 10, wherein:
the human body part comprises a pair of human legs;
the first orientation and the second orientation are selected from a group of orientations comprising:
  a pair of feet of the pair of human legs is oriented with heels on the heel indicia and toes pointing toward the electronic device;
  the pair of feet oriented with heels on the heel indicia, toes of a first foot of the pair of feet pointing toward the electronic device, and toes of a second foot of the pair of feet pointing substantially perpendicular with respect to the toes of the first foot;
  the pair of feet oriented with heels on the heel indicia, the toes of the second foot pointing toward the electronic device, and the toes of the second foot pointing substantially perpendicular with respect to the toes of the second foot;
  the pair of feet oriented with heels on the heel indicia, the toes of the second foot pointing opposite the electronic device, and the toes of the first foot pointing substantially perpendicular with respect to the toes of the second foot; and
  the pair of feet oriented with heels on the heel indicia, the toes of the first foot pointing opposite the electronic device, and the toes of the second foot pointing substantially perpendicular with respect to the toes of the first foot; and
further comprising detecting that the pair of human legs is in the first orientation, wherein capturing the first set of images comprises capturing the first set of images responsive to detecting that the pair of human legs is in the first orientation.

12. The method of claim 1, wherein the first set of images includes a plurality of images, and further comprising:
providing the plurality of images for presentation at a screen of the electronic device;
requesting user selection of a best image of the plurality of images to define the portion of the first set of images; and
determining the portion of the first set of images based at least in part on the user selection of the best image of the plurality of images.

13. The method of claim 1, further comprising:
providing the first set of images and the second set of images for presentation at a screen of the electronic device;
requesting user selection of individual images of the first set of images and the second set of images to define the portion of the first set of images and the second set of images; and
determining the portion of the first set of images and the second set of images based at least in part on the user selection of the individual images; and
responsive to an empty user selection:
  instructing capture, by the camera of the electronic device, of additional images for the first set of images of the human body part in the first orientation; and
  instructing capture, by the camera of the electronic device, of additional images for the second set of images of the human body part in the second orientation.

14. The method of claim 1, wherein:
capturing the first set of images is responsive to a first voice command instructing the camera to capture the first set of images;
capturing the second set of images is responsive to a second voice command instructing the camera to capture the second set of images; and
the electronic device includes a voice assistant.

15. The one or more non-transitory computer readable storage devices of claim 3, wherein the first set of images includes a plurality of images, and comprising computer-executable instructions that, when executed by the one or more processors, cause the one or more processors to perform operations further comprising:
- providing the plurality of images for presentation at a screen of the electronic device;
- requesting user selection of a best image of the plurality of images to define the portion of the first set of images; and
- determining the portion of the first set of images based at least in part on the user selection of the best image of the plurality of images.

16. The one or more non-transitory computer readable storage devices of claim 3, comprising computer-executable instructions that, when executed by the one or more processors, cause the one or more processors to perform operations further comprising:
- providing the first set of images and the second set of images for presentation at a screen of the electronic device;
- requesting user selection of individual images of the first set of images and the second set of images to define the portion of the first set of images and the second set of images; and
- determining the portion of the first set of images and the second set of images based at least in part on the user selection of the individual images; and
- responsive to an empty user selection:
  - instructing capture, by the camera of the electronic device, of additional images for the first set of images of the human body part in the first orientation; and
  - instructing capture, by the camera of the electronic device, of additional images for the second set of images of the human body part in the second orientation.

17. The one or more non-transitory computer readable storage devices of claim 3, wherein:
- the computer-executable instruction for capturing the first set of images is responsive to a first voice command instructing the camera to capture the first set of images;
- the computer-executable instruction for capturing the second set of images is responsive to a second voice command instructing the camera to capture the second set of images; and
- the electronic device includes a voice assistant.

18. The system of claim 6, wherein the set of orientation indicia are visible on a bottom section of the portable photo studio and comprise heel indicia, orientation indicia of a first type, and orientation indicia of a second type, and wherein the heel indicia, the orientation indicia of the first type, and the orientation indicia of the second type are divided into two reference indicium groups.

19. The system of claim 18, wherein:
- the human body part comprises a pair of human legs;
- the first orientation and the second orientation are selected from a group of orientations comprising:
  - a pair of feet of the pair of human legs is oriented with heels on the heel indicia and toes pointing toward the electronic device;
  - the pair of feet oriented with heels on the heel indicia, toes of a first foot of the pair of feet pointing toward the electronic device, and toes of a second foot of the pair of feet pointing substantially perpendicular with respect to the toes of the first foot;
  - the pair of feet oriented with heels on the heel indicia, the toes of the second foot pointing toward the electronic device, and the toes of the second foot pointing substantially perpendicular with respect to the toes of the second foot;
  - the pair of feet oriented with heels on the heel indicia, the toes of the second foot pointing opposite the electronic device, and the toes of the first foot pointing substantially perpendicular with respect to the toes of the second foot; and
  - the pair of feet oriented with heels on the heel indicia, the toes of the first foot pointing opposite the electronic device, and the toes of the second foot pointing substantially perpendicular with respect to the toes of the first foot; and
- further comprising detecting that the pair of human legs is in the first orientation, wherein capturing the first set of images comprises capturing the first set of images responsive to detecting that the pair of human legs is in the first orientation.

20. The system of claim 6, wherein:
- providing the first instructions and the second instructions comprises providing the first instructions and the second instructions via a speaker or a screen of the electronic device; and
- the first instructions and the second instructions are provided with respect to markings on a bottom section of the portable photo studio.

\* \* \* \* \*